United States Patent
Allen et al.

(10) Patent No.: US 6,541,258 B2
(45) Date of Patent: Apr. 1, 2003

(54) AAV SPLIT-PACKAGING GENES AND CELL LINES COMPRISING SUCH GENES FOR USE IN THE PRODUCTION OF RECOMBINANT AAV VECTORS

(75) Inventors: James M. Allen, Seattle, WA (US); Anthony M. Stepan, Seattle, WA (US); Tineka J. Quinton, Seattle, WA (US); Stephen D. Lupton, Seattle, WA (US)

(73) Assignee: Targeted Genetics Corporation, Seattle, WA (US)

( * ) Notice: Subject to any disclaimer, the term of this patent is extended or adjusted under 35 U.S.C. 154(b) by 0 days.

(21) Appl. No.: 08/981,172

(22) PCT Filed: Dec. 12, 1997

(86) PCT No.: PCT/US97/23247

§ 371 (c)(1),
(2), (4) Date: Dec. 12, 1997

(87) PCT Pub. No.: WO98/27204

PCT Pub. Date: Jun. 25, 1998

(65) Prior Publication Data

US 2002/0081721 A1 Jun. 27, 2002

Related U.S. Application Data

(60) Provisional application No. 60/041,609, filed on Dec. 18, 1996.

(51) Int. Cl.[7] .................. C12N 15/87; C12N 15/90; C12N 15/86; C12N 7/01; C12N 5/10

(52) U.S. Cl. .................. 435/455; 435/325; 435/366; 435/465; 435/320.1; 536/23.72

(58) Field of Search .................. 435/325, 320.1, 435/455, 463, 465, 366; 536/23.72

(56) References Cited

U.S. PATENT DOCUMENTS

| | | |
|---|---|---|
| 5,173,414 A | 12/1992 | Lebkowski et al. |
| 5,354,678 A | 10/1994 | Lebkowski et al. |
| 5,789,390 A * | 8/1998 | Descamps et al. ............ 514/44 |

FOREIGN PATENT DOCUMENTS

| | | |
|---|---|---|
| WO | WO 94/13788 | 6/1994 |
| WO | WO 95/06743 | 3/1995 |
| WO | WO 95/13365 | 5/1995 |
| WO | WO 95/13392 | 5/1995 |
| WO | WO 95/20671 | 8/1995 |
| WO | WO 96/17947 | 6/1996 |
| WO | WO 96/00587 | 11/1996 |

OTHER PUBLICATIONS

Berns, "Parvoviridae and Their Replication" *Virology*, 1743–1764, Raven Press (New York) (1990).
Carter, "Handbook of Parvoviruses," 1:169–228 (1989).
Carter, "Handbook of Parvoviruses," II:247–284, CRC Press, Boca Raton, FL (1989).
Carter, "Adeno–associated virus vectors" *Current Opinions in Biotechnology*, 3:533–539 (1992).
Chatterjee et al., "Vaccines 91," Cold Spring Harbor Laboratory Press, 85–89 (1991).
Chatterjee et al., "Dual–Target Inhibition of HIV–1 in Vitro by Means of an Aden–Associated Virus Antisense Vector" *Science*, 258:1485–1488 (1992).
Chejanovsky et al., "Mutagenesis of an AUG Codon in the Adeno–Associated virus rep Gene: Effects on Viral DNA replication" *Virology*, 173:120–128 (1989).
Egan et al., "Defective regulation of outwardly rectifying Cl⁻channels by protein kinase A corrected by insertion of CFTR" *Nature*, 358:581–584 (1992).
Flotte et al., "Gene Expression from Adeno–associated Virus vectors in Airway Epithelial Cells" *Am. J. Respir. Cell Mol. Biol.*, 7:349–356 (1992a).
Flotte et al., "Expression of the Cystic Fibrosis Transmembrane Conductance Regulator from a Novel Adeno–associated Virus Promoter" *J. Biol. Chem.*, 268:3781–3790 (1993a).
Flotte et al., "Stable in vivo expression of the cystic fibrosis transmembrane conductance regulator with an adeno–associated virus vector" *Proc. Natl. Acad. Sci. USA*, 93:10163–10167 (1993b).
Hermonat et al., "Use of adeno–associated virus as a mammalian DNA cloning vector: Transduction of neomycin resistance into mammalian tissue culture cells" *Proc. Natl. Acad. Sci. USA*, 81:6466–6470 (1984).
Hermonat et al., "Genetics of Adeno–Associated Virus: Isolation and Preliminary characterization of Adeno–Associated Virus Type 2 Mutants" *J. Virol.*, 51:329–339 (1984??).
Hölscher et al., "Cell Lines Inducibly Expressing the Adeno–Associated Virus (AAV) rep Gene: requirements for Productive Replication of rep–Negative AAV Mutants" *J. Virol.*, 68(1):7169–7177 (1994).
Hölscher et al., "High–Level Expression of Adeno–Associated Virus (AAV) Rep78 or Rep68 Protein Is Sufficient for Infectious–Particle Formation by a rep–Negative AAV Mutant" *J. Virol.*, 69:6880–6885 (1995).
Kaplitt et al., "Long–term gene expression and phenotypic correction using adeno–associated virus vectors in the mammalian brain" *Nature Genetics*, 8:148–154 (1994).
Khleif et al., "Inhibition of Cellular Transformation by the Adeno–Associated Virus rep Gene" *Virology*, 181:738–741 (1991).
Labow et al., "Adeno–Associated Virus Gene Expression Inhibits Cellular Transformation by Heterologous Genes" *Mol. Cell. Biol.*, 7:1320–1325 (1987).

(List continued on next page.)

Primary Examiner—Mary E. Mosher
(74) Attorney, Agent, or Firm—Morrison & Foerster LLP

(57) ABSTRACT

The present invention provides AAV "split-packaging" genes, and packaging cells comprising such genes, for use in the production of high titers of replication-incompetent recombinant AAV vectors that can be used to deliver transgenes of interest to a variety of mammalian cells.

21 Claims, 2 Drawing Sheets

OTHER PUBLICATIONS

Laughlin et al., "Cloning of infectious adeno–associated virus genomes in bacterial plasmids" *Gene*, 23:65–73 (1983).

Laughlin et al., "Spliced adenovirus–Associated virus RNA" *Proc. Natl. Acad. Sci. USA*, 76:5567–5571 (1979).

McLaughlin et al., "Adeno–Associated Virus General Transduction Vectors: Analysis of Proviral Structures" *J. Virol.* 62:1963–1973 (1988).

Mendelson et al., "Expression and Rescue of a Nonselected Marker from an Integrated AAV Vector" *Virology*, 166:154–165 (1988).

Muro–Cacho et al., "Gene Transfer in Human Lymphocytes Using a Vector Based on Adeno–Associated Virus" J. Immunotherapy, 11:231–237 (1992).

Muzyczka, *Curr. Topics in Microbiol. and Immunol.*, 158:97–129 (1992).

Samulski et al., "A Recombinant Plasmid from Which an Infectious Adeno–Associated Virus Genome Can Be Excised In Vitro and Its Use To Study Viral Replication" *J. Virol.*, 61(10):3096–3101 (1987).

Samulski et al., "Helper–Free Stocks of Recombinant Adeno–Associated Viruses: Normal Integration Does Not Require Viral Gene Expression" *J. Virol.*, 63(9):3822–3828 (1989).

Samulski et al., "Cloning of adeno–associated virus into pBR322: Rescue of intact virus from the recombinant plasmid in human cells" *Proc. Natl. Acad. Sci. USA*, 79:2077–2081 (1982).

Senapathy et al., "Molecular cloning of Adeno–associated Virus Variant Genomes and Generation of Infectious Virus by Recombination in Mammalian Cells" *J. Biol. Chem.*, 259(7):4661–4666 (1984).

Srivastava et al., "Nucleotide Sequence and Organization of the Adeno–Associated Virus 2 Genome" *J. Virol.*, 45(2):555–564 (1983).

Srivastava et al., "Construction of a recombinant human parvovirus B19: Adeno–associated virus 2 (AAV) DNA inverted terminal repeats are functional in an AAV–B19 hybrid virus" *Proc. Natl. Acad. Sci. USA*, 86:8078–8082 (1989).

Tratschin et al., "Negative and Positive Regulation in Trans of Gene Expression from Adeno–Associated Virus Vectors in Mammalian Cells by a Viral rep Gene Product" *Mol. Cell. Biol.* 6(8):2884–2894 (1986).

Tratschin et al., "A Human Parvovirus, Adeno–Associated Virus, as a Eucaryotic Vector: Transient Expression and Encapsidation of the Procaryotic Gene for Chloramphenicol Acetyltransferase" *Mol. Cell. Biol.*, 4:2072–2081 (1984b).

Tratschin et al., "Genetic analysis of Adeno–Associated Virus: Properties of Deletion Mutants constructed In Vitro and Evidence for an Adeno–Associated Virus Replication Function" *J. of Virol.* 51(3):611–619 (1984).

Tratschin et al., "Adeno–Associated virus Vector for High–Frequency Integration, Expression, and Rescue of Genes in Mammalian Cells" *Mol. Cell. Biol.*, 5(11):3251–3260 (1985).

Vincent et al., "Vaccines 90," Cold Spring Harbor Laboratory Press,353–359 (1990).

Walsh et al., "regulated high level expression of a human γ–globin gene introduced into erythroid cells by an adeno–associated virus vector" *Proc. Natl. Acad. Sci. USA*, 89:7257–7261 (1992).

Wayne et al., "Genomic Organization of Alpha Satellite DNA on Human Chromosome 7: Evidence for Two Distinct Alphoid Domains on a Single Chromosome" *Mol. Cell. Biol.*, 7(1):349–356 (1987).

Wong et al., "Vaccines 91," Cold Spring Harbor Laboratory Press, 183–189 (1991).

* cited by examiner

AAV SPLIT-PACKAGING GENES AND CELL LINES COMPRISING SUCH GENES FOR USE IN THE PRODUCTION OF RECOMBINANT AAV VECTORS

CROSS-REFERENCE TO RELATED APPLICATIONS

The application is the national phase of PCT Application No. PCT/US97/23247, filed Dec. 12, 1997; which is a continuation of United States Provisional Application No. 60/041,609, (which was converted from U.S. application Ser. No. 08/769,728) filed Dec. 18, 1996.

TECHNICAL FIELD OF THE INVENTION

This invention relates to materials and methods used for the generation of high titers of viral vectors, particularly recombinant adeno-associated virus (AAV) vectors. More specifically, the invention relates to AAV split-packaging genes, and cell lines comprising such genes, for use in the production of high titers of replication-incompetent AAV vectors.

BACKGROUND

Vectors based on adeno-associated virus (AAV) are believed to have utility for gene therapy but a significant obstacle has been the difficulty in generating such vectors in amounts that would be clinically useful for human gene therapy applications. This is a particular problem for in vivo applications such as direct delivery to the lung. Another important goal in the gene therapy context, discussed in more detail herein, is the production of vector preparations that are essentially free of replication-competent virions. The following description briefly summarizes studies involving adeno-associated virus and AAV vectors, and then describes a number of novel improvements according to the present invention that are useful for efficiently generating high titer recombinant AAV vector (rAAV) preparations suitable for use in gene therapy.

Adeno-associated virus is a defective parvovirus that grows only in cells in which certain functions are provided by a co-infecting helper virus. General reviews of AAV may be found in, for example, Carter, 1989, *Handbook of Parvoviruses*, Vol. I, pp. 169–228, and Berns, 1990, *Virology*, pp. 1743–1764, Raven Press, (New York). Examples of co-infecting viruses that provide helper functions for AAV growth and replication are adenoviruses, herpesviruses and, in some cases, poxviruses such as vaccinia. The nature of the helper function is not entirely known but it appears that the helper virus indirectly renders the cell permissive for AAV replication. This belief is supported by the observation that AAV replication may occur at low efficiency in the absence of helper virus co-infection if the cells are treated with agents that are either genotoxic or that disrupt the cell cycle.

Although AAV may replicate to a limited extent in the absence of helper virus in these unusual conditions more generally infection of cells with AAV in the absence of helper functions results in the proviral AAV genome integrating into the host cell genome. If these cells are superinfected with a helper virus such as adenovirus, the integrated AAV genome can be rescued and replicated to yield a burst of infectious progeny AAV particles. The fact that integration of AAV appears to be efficient suggests that AAV would be a useful vector for introducing genes into cells for uses such as human gene therapy.

AAV has a very broad host range without any obvious species or tissue specificity and can replicate in virtually any cell line of human, simian or rodent origin provided that an appropriate helper is present. AAV is also relatively ubiquitous and has been isolated from a wide variety of animal species including most mammalian and several avian species.

AAV is not associated with the cause of any disease. Nor is AAV a transforming or oncogenic virus, and integration of AAV into the genetic material of human cells generally does not cause significant alteration of the growth properties or morphological characteristics of the host cells. These properties of AAV also recommend it as a potentially useful human gene therapy vector because most of the other viral systems proposed for this application, such as retroviruses, adenoviruses, herpesviruses, or poxviruses, are disease-causing.

AAV particles are comprised of a proteinaceous capsid having three capsid proteins, VP1, VP2 and VP3, which enclose a DNA genome. The AAV DNA genome is a linear single-stranded DNA molecule having a molecular weight of about $1.5 \times 10^6$ daltons and a length of approximately 4680 nucleotides. Individual particles package only one DNA molecule strand, but this may be either the "plus" or "minus" strand. Particles containing either strand are infectious and replication occurs by conversion of the parental infecting single strand to a duplex form and subsequent amplification of a large pool of duplex molecules from which progeny single strands are displaced and packaged into capsids. Duplex or single-strand copies of AAV genomes can be inserted into bacterial plasmids or phagemids and transfected into adenovirus-infected cells; these techniques have facilitated the study of AAV genetics and the development of AAV vectors.

The AAV genome, which encodes proteins mediating replication and encapsidation of the viral DNA, is generally flanked by two copies of inverted terminal repeats (ITRs). In the case of AAV2, for example, the ITRs are each 145 nucleotides in length, flanking a unique sequence region of about 4470 nucleotides that contains two main open reading frames for the rep and cap genes (Srivastava et al., 1983, *J. Virol.*, 45:555–564; Hermonat et al., *J. Virol.*51:329–339; Tratschin et al., 1984a, *J. Virol.*, 51:611–619). The AAV2 unique region contains three transcription promoters p5, p19, and p40 (Laughlin et al., 1979, *Proc. Natl. Acad. Sci. USA*, 76:5567–5571) that are used to express the rep and cap genes. The ITR sequences are required in cis and are sufficient to provide a functional origin of replication (ori), signals required for integration into the cell genome, and efficient excision and rescue from host cell chromosomes or recombinant plasmids. It has also been shown that the ITR can function directly as a transcription promoter in an AAV vector (Flotte et al., 1993, supra).

The rep and cap gene products are required in trans to provide functions for replication and encapsidation of viral genome, respectively. The rep gene is expressed from two promoters, p5 and p19, and produces four proteins. Transcription from p5 yields an unspliced 4.2 kb mRNA encoding a first Rep protein (Rep78), and a spliced 3.9 kb mRNA encoding a second Rep protein (Rep68). Transcription from p19 yields an unspliced mRNA encoding a third Rep protein (Rep52), and a spliced 3.3 kb mRNA encoding a fourth Rep protein (Rep40). Thus, the four Rep proteins all comprise a common internal region sequence but differ in their amino and carboxyl terminal regions. Only the large Rep proteins (i.e. Rep78 and Rep68) are required for AAV duplex DNA replication, but the small Rep proteins (i.e. Rep52 and Rep40) appear to be needed for progeny, single-strand DNA accumulation (Chejanovsky & Carter, 1989, *Virology* 173:120–128). Rep68 and Rep78 bind specifically to the hairpin conformation of the AAV ITR and possess several enzyme activities required for resolving replication at the AAV termini. Rep52 and Rep40 have none of these properties. Recent reports by C. Hölscher et al. (1994, *J. Virol.* 68:7169–7177; and 1995, *J. Virol.* 69:6880–6885) suggest that expression of Rep 78 or Rep 68 may in some circumstances be sufficient for infectious particle formation.

The Rep proteins, primarily Rep78 and Rep68, also exhibit pleiotropic regulatory activities including positive and negative regulation of AAV genes and expression from some heterologous promoters, as well as inhibitory effects on cell growth (Tratschin et al., 1986, *Mol. Cell. Biol.* 6:2884–2894; Labow et al., 1987, *Mol. Cell. Biol.,* 7:1320–1325; Klileifet al., 1991, *Virology,* 181:738–741). The AAV p5 promoter is negatively auto-regulated by Rep78 or Rep68 (Tratschin et al., 1986, *Mol. Cell. Biol.* 6:2884–2894). Due to the inhibitory effects of expression of rep on cell growth, constitutive expression of rep in cell lines has not been readily achieved. For example, Mendelson et al. (1988, *Virology,* 166:154–165) reported very low expression of some Rep proteins in certain cell lines after stable integration of AAV genomes.

The capsid proteins VP1, VP2, and VP3 share a common overlapping sequence, but VP1 and VP2 contain additional amino terminal sequences. All three proteins are encoded by the same cap gene reading frame typically expressed from a spliced 2.3 kb mRNA transcribed from the p40 promoter. VP2 and VP3 can be generated from this mRNA by use of alternate initiation codons. Generally, transcription from p40 yields a 2.6 kb precursor mRNA which can be spliced at alternative sites to yield two different transcripts of about 2.3 kb. VP2 and VP3 can be encoded by either transcript (using either of the two initiation sites), whereas VP1 is encoded by only one of the transcripts. VP3 is the major capsid protein, typically accounting for about 90% of total virion protein. VP1 is coded from a minor mRNA using a 3' donor site that is 30 nucleotides upstream from the 3' donor used for the major mRNA that encodes VP2 and VP3. All three proteins are required for effective capsid production. Mutations which eliminate all three proteins (Cap-negative) prevent accumulation of single-strand progeny AAV DNA, whereas mutations in the VP1 amino-terminus ("Lip-negative" or "Inf-negative") can permit assembly of single-stranded DNA into particles but the infectious titer is greatly reduced.

The genetic analysis of AAV that was highlighted above was largely based upon mutational analysis of AAV genomes cloned into bacterial plasmids. In early work, molecular clones of infectious genomes of AAV were constructed by insertion of double-strand molecules of AAV into plasmids by procedures such as GC tailing (Samulski et al., 1982, *Proc. Natl. Acad. Sci. USA,* 79:2077–2081), addition of synthetic linkers containing restriction endonuclease cleavage sites (Laughlin et al., 1983, *Gene,* 23:65–73) or by direct, blunt-end ligation (Senpathy & Carter, 1984, *J. Biol. Chem.,* 259:4661–4666). Transfection of such AAV recombinant plasmids into mammalian cells that were also infected with an appropriate helper virus, such as adenovirus, resulted in rescue and excision of the AAV genome free of any plasmid sequence, replication of the rescued genome and generation of progeny infectious AAV particles. This provided the basis for performing genetic analysis of AAV as summarized above and permitted construction of AAV transducing vectors.

Based on the genetic analysis, the general principles of AAV vector construction were defined as reviewed recently (Carter, 1992, *Current Opinions in Biotechnology,* 3:533–539; Muzyczka, 1992, *Curr. Topics in Microbiol. and Immunol.,* 158:97–129). AAV vectors are generally constructed in AAV recombinant plasmids by substituting portions of the AAV coding sequence with foreign DNA to generate a recombinant AAV (rAAV) vector or "pro-vector". In the vector, the terminal (ITR) portions of the AAV sequence must generally be retained intact because these regions are generally required in cis for several functions, including excision from the plasmid after transfection, replication of the vector genome and integration and rescue from a host cell genome. In some situations, providing a single ITR may be sufficient to carry out the functions normally associated with two wild-type ITRs (see, e.g., Samulski, R. J. et al., WO 94/13788, published Jun. 23, 1994). The vector can then be packaged into an AAV particle to generate an AAV transducing virus by transfection of the vector into cells that are infected by an appropriate helper virus such as adenovirus or herpesvirus; provided that, in order to achieve replication and encapsidation of the vector genome into AAV particles, the vector must be complemented for any AAV functions required in trans, particularly rep and cap, that were deleted in construction of the vector.

Such AAV vectors are among a small number of recombinant virus vector systems which have been shown to have utility as in vivo gene transfer agents (reviewed in Carter, 1992, *Current Opinion in Biotechnology,* 3:533–539; Muzcyzka, 1992, *Curr. Top. Microbiol. Immunol.* 158:97–129 ) and thus are potentially of great importance for human gene therapy. AAV vectors are capable of high-frequency transduction and expression in a variety of cells including cystic fibrosis (CF) bronchial and nasal epithelial cells (see, e.g., Flotte et al., 1992a, *Am. J. Respir. Cell Mol. Biol.* 7:349–356; Egan et al., 1992, *Nature,* 358:581–584; Flotte et al., 1993a, *J. Biol. Chem.* 268:3781–3790; and Flotte et al., 1993b, *Proc. Natl. Acad. Sci. USA,* 93:10163–10167); human bone marrow-derived erythroleukemia cells (see, e.g., Walsh et al., 1992, *Proc. Natl. Acad. Sci. USA,* 89:7257–7261); as well as brain, eye and muscle cells. AAV may not require active cell division for transduction and expression which would be another clear advantage over retroviruses, especially in tissues such as the human airway epithelium where most cells are terminally differentiated and non-dividing.

There are at least two desirable features of any AAV vector designed for use in human gene therapy. First, the transducing vector must be generated at titers sufficiently high to be practicable as a delivery system. This is especially important for gene therapy stratagems aimed at in vivo delivery of the vector. For example, it is likely that for many desirable applications of AAV vectors, such as treatment of cystic fibrosis by direct in vivo delivery to the airway, the required dose of transducing vector may be in excess of $10^{10}$ particles. Secondly, the vector preparations are preferably essentially free of wild-type AAV virus (or any replication-competent AAV). The attainment of high titers of AAV vectors has been difficult for several reasons including preferential encapsidation of wild-type AAV genomes (if they are present or generated by recombination), and the difficulty in generating sufficient complementing functions such as those provided by the wild-type rep and cap genes. Useful cell lines expressing such complementing functions have been especially difficult to generate, in part because of pleiotropic inhibitory functions associated with the rep gene products. Thus, cell lines in which the rep gene is integrated and expressed tend to grow slowly or express rep at very low levels.

The first AAV vectors described contained foreign reporter genes such as neo, cat or dhfr expressed from AAV transcription promoters or an SV40 promoter (Tratschin et al., 1984b, *Mol. Cell. Biol.* 4:2072–2081; Hermonat & Muzyczka, 1984, *Proc. Natl. Acad. Sci. USA,* 81:6466–6470; Tratschin et al., 1985, *Mol. Cell. Biol.* 5:3251–3260; McLaughlin et al., 1988, *J. Virol,* 62:1963–1973; Lebkowski et al., 1988 *Mol. Cell. Biol.,* 7:349–356). These vectors were packaged into AAV-transducing particles by co-transfection into adenovirus-infected cells together with a second "packaging plasmid" containing the AAV rep and cap genes expressed from the wild-type AAV transcription promoters. Several strategies have been employed in attempts to prevent encapsidation of the packaging plasmid. In some cases, (Hermonat & Muzyczka, 1984; McLaughlin et al., 1988) a large region of bacteriophage lambda DNA was inserted into the packaging plasmid within the AAV sequence to generate an oversized genome that could not be packaged. In other cases, (Tratschin et al., 1984b; Tratschin et al., 1985, Lebkowski et al., 1988), the packaging plasmid had deleted the ITR regions of AAV so that it could not be excised and replicated and thus could not be packaged. All of these approaches failed to prevent generation of particles containing replication-competent AAV DNA and also failed to generate effective high titers of AAV transducing particles. Indeed, titers of not more than $10^4$ infectious particles per ml were cited by Hermonat & Muzyczka, 1984.

In many studies, the presence of overlapping homology between AAV sequences present in the vector and packaging plasmids resulted in the production of replication-competent AAV particles. It was shown by Senapathy and Carter (1984, *J. Biol. Chem.* 259:4661–4666) that the degree of recombination in such a system is approximately equivalent to the degree of sequence overlap. It was suggested in a review of the early work (Carter 1989, *Handbook of Parvoviruses*, Vol. II, pp. 247–284, CRC Press, Boca Raton, Fla.) that titers of $10^6$ infectious particles per ml might be obtained, but this was based on the above-cited studies in which large amounts of replication-competent AAV contaminated the vector preparation. Such vector preparations containing replication-competent AAV will generally not be preferred for human gene therapy. Furthermore, these early vectors exhibited low transduction efficiencies and did not transduce more than 1 or 2% of cells in cultures of various human cell lines even though the vectors were supplied at multiplicities of up to 50,000 particles per cell. This may have reflected in part the contamination with replication-competent AAV particles and the presence of the AAV rep gene in the vector. Furthermore, Samulski et al. (1989, *J. Virol.* 63:3822–3828) showed that the presence of wild-type AAV significantly enhanced the yield of packaged vector. Thus, in packaging systems where the production of wild-type AAV is eliminated, the yield of packaged vector may actually be decreased. Nevertheless, for use in any human clinical application it will be preferable to essentially eliminate production of replication-competent AAV.

Additional studies (McLaughlin et al., 1988; Lebkowski et al., 1988) attempting to generate AAV vectors lacking the AAV rep or cap genes still generated replication-competent AAV and still produced very low transduction frequencies on human cell lines. Thus, McLaughlin et al., 1988 reported that AAV rep-negative cap-negative vectors containing the neo gene packaged with the same packaging plasmid used earlier by Hermonat & Muzyczka (1984) still contained replication-competent AAV. As a consequence, it was only possible to use this virus at a multiplicity of 0.03 particles per cell (i.e., 300 infectious units per 10,000 cell) to avoid double hits with vector and wild-type particles. Thus, when 32,000 cells were infected with 1000 infectious units, an average of 800 geneticin-resistant colonies was obtained. Although this was interpreted as demonstrating that the virus was capable of yielding a transduction frequency of 80%, in fact only 2.5% of the cells were transduced. Thus the effectively useful titer of this vector was limited. Furthermore, this study did not demonstrate that the actual titer of the vector preparation was any higher than those obtained previously by Hermonat & Muzyczka (1984). Similarly, Lebkowski et al., 1988, packaged AAV vectors which did not contain either a rep or cap gene, using an ori-negative packaging plasmid (pBa1A) identical to that used earlier by Tratschin et al., (1984b, 1985), and reported transduction frequencies that were similarly low, in that for several human cell lines not more than 1% of the cells could be transduced to geneticin resistance even with their most concentrated vector stocks. Lebkowski et al., (1988) did not report the actual vector titers in a meaningful way but the biological assays, showing not more than 1% transduction frequency when $5 \times 10^6$ cells were exposed to three ml of vector preparation, indicate that the titer was less than $2 \times 10^4$ geneticin resistant units per ml. Also, the pBa1A packaging plasmid contains overlapping homology with the ITR sequence in the vector and can lead to generation of replication-competent AAV by homologous recombination.

Laface et al. (1988) used the same vector as that used by Hermonat & Muzyczka (1984) prepared in the same way and obtained a transduction frequency of 1.5% in murine bone marrow cultures, again showing very low titer.

Samulski et al. (1987, *J. Virol.,* 61:3096–3101) constructed a plasmid called pSub201 which contained an intact AAV genome in a bacterial plasmid but which had a deletion of 13 nucleotides at the extremity of each ITR and thus was rescued and replicated less efficiently than other AAV plasmids that contained the entire AAV genome. Samulski et al. (1989, *J. Virol.,* 63:3822–3828) constructed AAV vectors based on pSub201 but deleted for rep and cap and containing either a hyg or neo gene expressed from an SV40 early gene promoter. They packaged these vectors by co-transfection with a packaging plasmid called pAAV/Ad which consisted of the entire AAV nucleotide sequence from nucleotide 190 to 4490 enclosed at either end with one copy of the adenovirus ITR. In this packaging plasmid the AAV rep and cap genes were expressed from their native AAV promoters (i.e. p5, p19 and p40, as discussed above). The function of the adenovirus ITR in pAAV/Ad was thought to enhance the expression level of AAV capsid proteins. However, rep is expressed from its homologous promoter and is negatively regulated and thus its expression is limited. Using their encapsidation system, Samulski et al. generated AAV vector stocks that were substantially free of replication-competent AAV but had transducing titers of only $3 \times 10^4$ hygromycin-resistant units per ml of supernatant. When a wild-type AAV genome was used in the packaging plasmid, the titer of the AAV vector prep was increased to $5 \times 10^4$ hygromycin-resistant units per ml. The low titer produced in this system thus appears to have been due in part to the defect in the ITR sequences of the basic pSub201 plasmid used for vector construction and in part due to limiting expression of AAV genes from pAAV/Ad. In an attempt to increase the titer of the AAVneo vector preparation, Samulski et al. generated vector stocks by transfecting, in bulk, thirty 10-cm dishes of 293 cells and concentrating the vector stock by banding in CsCl. This produced an AAVneo vector stock containing a total of $10^8$ particles as measured by a DNA dot-blot hybridization assay. When this vector stock was used at multiplicities of up to 1,000 particles per cell, a transduction frequency of 70% was obtained. This suggests that the particle-to-transducing ratio is about 500 to 1,000 particles since at the ratio of one transducing unit per cell the expected proportion of cells that should be transduced is 63% according to the Poisson distribution.

Although the system of Samulski et al. (1989), using the vector plasmid pSub201 and the packaging plasmid pAAV/Ad, did not have overlapping AAV sequence homology between the two plasmids, there is overlapping homology at the XbaI sites and recombination of these sites can lead to the generation of complete replication-competent AAV. That is, although overlapping homology of AAV sequence is not present, the complete AAV sequence is contained within the two plasmids and the plasmids share a short (non-AAV) sequence that might facilitate recombination to generate replication-competent AAV, which is undesirable. That this class of recombination occurs in AAV plasmids was shown by Senapathy & Carter (1984, J. Biol. Chem. 259:466–4666). Given the problems of low titer, and the capability of generating wild-type recombinants, the system described by Samulski et al., 1989, does not have practical utility for human gene therapy.

Several other reports have described AAV vectors. For example, Srivastava et al., (1989, Proc. Natl. Acad. Sci. USA, 86:8078–8082) described an AAV vector based on the pSub201 plasmid of Samulski et al. (1987), in which the coding sequences of AAV were replaced with the coding sequences of another parvovirus, B19. This vector was packaged into AAV particles using the pAAV/Ad packaging plasmid to generate a functional vector, but titers were not reported. This system was based on pSub201 and thus suffers from the defect described above for this plasmid. Second, the vector and the packaging plasmid contained overlapping AAV sequences (the ITR regions) and thus recombination yielding contaminating wild-type virus is highly likely.

Chatterjee et al. (1991, Vaccines 91, Cold Spring Harbor Laboratory Press, pp. 85–89), Wong et al. (1991, Vaccines 91, Cold Spring Harbor Laboratory Press, pp. 183–189), and Chatterjee et al. (1992, Science, 258:1485–1488) describe AAV vectors designed to express antisense RNA directed against infectious viruses such as HIV or Herpes simplex virus. However, these authors did not report any titers of their AAV vector stocks. Furthermore, they packaged their vectors using an ori-negative packaging plasmid analogous to that used by Tratschin et al. (1984b, 1985) containing the BalA fragment of the AAV genome and therefore their packaging plasmid contained AAV vector sequences that have homology with AAV sequences that were present in their vector constructs. This will also lead to generation of replication-competent AAV. Thus, Chatterjee et al., and Wong et al., used a packaging system known to give only low titer and which can lead to generation of replication-competent AAV genomes because of the overlapping homology in the vector and packaging sequences.

Other reports have described the use of AAV vectors to express genes in human lymphocytes (Muro-Cacho et al., 1992, J. Immunotherapy, 11:231–237) or a human erythroid leukemia cell line (Walsh et al., 1992, Proc. Natl. Acad. Sci. USA, 89:7257–7261) with vectors based on the pSub201 vector plasmid and pAAV/Ad packaging plasmid. Again, titers of vector stocks were not reported and were apparently low because a selective marker gene was used to identify those cells that had been successfully transduced with the vector.

Transduction of human airway epithelia cells, grown in vitro from a cystic fibrosis patient, with an AAV vector expressing the selective marker gene neo from the AAV p5 promoter was reported (Flotte et al., 1992, Am. J. Respir. Cell. Mol. Biol. 7:349–356). In this study the AAVneo vector was packaged into AAV particles using the pAAV/Ad packaging plasmid. Up to 70% of the cells in the culture could be transduced to geneticin resistance and the particle-to-transducing ratio was similar to that reported by Samulski et al. (1989). Thus to obtain transduction of 70% of the cells, a multiplicity of up to several hundred vector particles per cell was required. Transduction of human airway epithelial cells in in vitro culture using an AAV transducing vector that expressed the cystic fibrosis transmembrane conductance regulator (CFTR) gene from the AAV ITR promoter showed that the cells could be functionally corrected for the electrophysiological defect in chloride channel function that exists in cells from cystic fibrosis patients (Egan et al., Nature, 1992, 358:581–584; Flotte et al., J. Biol. Chem.268:3781–3790).

The above-cited studies suggest that AAV vectors have potential utility as vectors for treatment of human disease by gene therapy. However, the difficulty in generating sufficient amounts of AAV vectors has been a severe limitation on the development of human gene therapy using AAV vectors. One aspect of this limitation is that there have been very few studies using AAV vectors in in vivo animal models (see, e.g., Flotte et al., 1993b; and Kaplitt et al., 1994, Nature Genetics 8:148–154). This is generally a reflection of the difficulty associated with generating sufficient amounts of AAV vector stocks having a high enough titer to be useful in analyzing in vivo delivery and gene expression.

One of the limiting factors for AAV gene therapy has been the relative inefficiency of the vector packaging systems that have been used. In the absence of suitable cell lines expressing sufficient levels of the AAV trans complementing functions, such as rep and cap, packaging of AAV vectors has been achieved in adenovirus-infected cells by co-transfection of a packaging plasmid and a vector. The efficiency of this process is expected to be limited by the efficiency of transfection of each of the plasmid constructs, and by the low level of expression of Rep proteins from the packaging plasmids described to date. Each of these problems appears to relate to the biological activities of the AAV Rep proteins which are known to be associated with pleiotropic inhibitory effects. In addition, as noted above, all of the packaging systems described above have the ability to generate replication-competent AAV by recombination.

The difficulty in generating cell lines stably expressing functional Rep apparently reflects a cytotoxic or cytostatic function of Rep as shown by the inhibition, by Rep protein, of neo-resistant colony formation (Labow et al., 1987; Trempe et al., 1991). This also appears to relate to the tendency of Rep to reverse the immortalized phenotype in cultured cells, which has made the production of cell lines stably expressing functional rep extremely difficult. Several attempts to generate cell lines expressing rep have been made. Mendelson et al., (1988, Virology, 166:154–165) reported obtaining in one cell line some low level expression of AAV Rep52 protein but no Rep78 or Rep68 protein after stable transfection of Hela or 293 cells with plasmids containing an AAV rep gene. Because of the absence of Rep78 and Rep68 proteins, vector could not be produced in the cell line. Another cell line made a barely detectable amount of Rep78 which was nonfunctional.

Vincent et al. (1990, Vaccines 90, Cold Spring Harbor Laboratory Press, pp. 353–359) attempted to generate cell lines containing the AAV rep and cap genes expressed from the normal AAV promoters, but these attempts were not successful either because the vectors were contaminated with a 100-fold excess of wild-type AAV particles or because the vectors were produced at only very low titers of less than $4 \times 10^3$ infectious particles.

Other variations that have been proposed include systems based on the production of AAV Cap proteins that might be used to reconstitute AAV particles, e.g. by assembly in vitro (see, e.g., WO 96/00587, published Nov. 1, 1996); systems employing AAV rep-cap genes on a helper virus (see, e.g., WO 95/06743, published Mar. 9, 1995); and systems employing helper viruses from non-human mammals (see, e.g., WO 95/20671, published Aug. 3, 1995).

In yet another approach, Lebkowski et al. (U.S. Pat. No. 5,173,414, issued Dec. 22, 1992) constructed cell lines containing AAV vectors in an episomal plasmid. These cell lines could then be infected with adenovirus and transfected with the trans-complementing AAV functions rep and cap to generate preparations of AAV vector. It is claimed that this allows higher titers of AAV stocks to be produced. However, in the examples shown, the only information relative to titer that is shown is that one human cell line, K562, could be transduced at efficiencies of only 1% or less, which does not indicate high titer production of any AAV vector. In this system the vector is carried as an episomal (unintegrated) construct, and it is stated that integrated copies of the vector are not preferred. In a subsequent patent (U.S. Pat. No. 5,354,678, issued Oct. 11, 1994), Lebkowski et al. introduce rep and cap genes into the cell genome but the method again requires the use of episomal AAV transducing vectors comprising an Epstein-Barr virus nuclear antigen (EBNA) gene and an Epstein-Barr virus latent origin of replication; and, again, the only information relative to titer indicated that it was fairly low.

The approach to packaging of rAAV vectors described by Lebkowski et al., 1992, can be undesirable in several ways. First, maintaining the rAAV vector as an unintegrated, high copy number episomal plasmid in a cell line is not desirable because the copy number per cell cannot be rigorously controlled and episomal DNA is much more likely to undergo rearrangement leading to production of defective vectors. Secondly, in this system, the vector must still be packaged by infecting the cell line with adenovirus and introducing a plasmid containing the AAV rep and cap genes. The plasmid used by Lebkowski et al. (1992) was again pBal A, which has overlapping homology with the vector ITR sequences and can result in generation of replication-competent AAV. Third, in the pBa1A packaging plasmid used by Lebkowski et al., 1988, 1992, the rep gene is expressed from its homologous p5 promoter and, since rep is generally negatively autoregulated, this would tend to limit rep expression.

The problem of suboptimal levels of rep expression after plasmid transfection thus also relates to another biological activity of these proteins. There is evidence (Tratschin et al., 1986, *Mol. Cell. Biol.* 6:2884–2894) that AAV Rep proteins down-regulate their own expression from the AAV-p5 promoter which has been used in the various previously described packaging constructs such as pAAV/Ad (Samulski et al., 1989) or pBa1A (Lebkowski et al., 1988, 1992).

Another attempt to develop cell lines expressing functional rep activity was recently published by Hölscher et al. (1994, *J. Virol.* 68:7169–7177). They described the generation of cell lines in which rep was placed under control of a glucocorticoid-responsive MMTV promoter. Although they observed particle formation, the particles were apparently noninfectious. Additional experiments indicated that the defect was quite fundamental; namely, there was virtually no accumulation of single-stranded rAAV DNA in the cells. Production of infectious particles required an additional transient transfection with constitutive highly-expressed rep constructs (i.e. they had to "add back" Rep activity to cells that were supposed to be able to provide it themselves). Several other approaches to generating AAV packaging cell lines have also been described recently, see, e.g., T. Flotte et al., WO 95/13365 (Targeted Genetics Corporation and Johns Hopkins University); J. Trempe et al., WO 95/13392 (Medical College of Ohio); and J. Allen, WO 96/17947 (Targeted Genetics Corporation).

There is a significant need for methods that can be used to efficiently generate rAAV vectors that are essentially free of wild-type or other replication-competent AAV; and a corresponding need for cell lines that can be used to effectively generate such rAAV vectors.

SUMMARY OF THE INVENTION

One of the basic challenges for gene therapy has been the development of strategies for transduction of cells and tissues which cannot be easily manipulated ex vivo or which are not actively dividing. AAV vectors can achieve in vivo gene transfer in the respiratory tract, for example, but high titers are critical so as to allow for the delivery of sufficiently high multiplicity of vector in as small a volume as possible. In addition, prior art techniques that do not substantially eliminate the generation of replication-competent AAV ("rcA") are generally unsatisfactory. In addition, stable, AAV packaging cell lines have been elusive, mainly due to the activities of Rep proteins, which tend to down-regulate their own expression and can negatively affect the lost cell. These concerns, particularly when considered in combination, make packaging methodology of central importance in AAV-based gene therapy applications. Although a number of suggestions have been proposed in the art, very few of them have actually been tested, and many that have are practically inadequate for reasons as dicussed above.

The closely-coupled and tightly-regulated rep and cap functions characteristic of wild-type AAV, and various prior packaging systems, are uncoupled and reorganized in the packaging cell lines of the present invention. The inventors have found that their redesigned system is capable of providing significantly greater quantities of heat-stable recombinant AAV vectors, while at the same time greatly reducing the possibility of generating replication-competent AAV particles.

1. A mammalian cell useful for high efficiency packaging of a recombinant adeno-associated virus (rAAV) vector, said cell comprising at least one copy of each of the following AAV split-packaging genes:

(i) an AAV split-cap gene, wherein said split-cap gene is uncoupled from Rep78-specific sequences of an AAV rep gene, and wherein said split-cap gene is operably linked to a heterologous promoter; and (ii) an AAV rep78 gene, wherein said rep78 gene is uncoupled from Cap-specific sequences of an AAV cap gene, and wherein said rep78 gene is operably linked to a heterologous promoter. Preferably, the rep78 gene is operably linked to an inducible promoter; the split-cap gene can be operably linked to an inducible promoter or to a constitutive promoter.

Important properties of such cells include the fact that they can generate high titers of infectious rAAV particles, as illustrated below, and they have a greatly reduced likelihood of generating replication-competent AAV. Indeed, the frequency of generating rcA is expected to be less than 1 in $10^8$ particles generated, and is likely to be much less frequent than that (as described below).

2. A mammalian cell according to embodiment 1, further comprising an AAV rep52 gene, wherein said rep52 gene is uncoupled from Rep78-specific sequences of an AAV rep gene, and wherein said rep52 gene is operably linked to a promoter, preferably a heterologous promoter. The use of both split-cap and rep52 genes has been found to result in the generation of substantially increased amounts of infectious rAAV particles, and the resulting particles are heat stable to at least 56 degrees Celsius for one hour, even when packaging an "over-sized" rAAV vector (i.e. larger than the normal AAV genome size) such as the CFTR vector exemplified below.

3. A mammalian cell according to one of the preceding embodiments, wherein at least one of said promoters is an inducible heterologous promoter; preferably at least the rep78 promoter is an inducible heterologous promoter; most preferably, it is a helper-virus-inducible promoter. The rep52 and split-cap genes can also be linked to heterologous promoters, including helper-virus-inducible promoters.

4. A mammalian cell according to one of the preceding embodiments, wherein at least one of said AAV split-packaging genes is operably linked to a heterologous enhancer; preferably, at least two of said AAV split-packaging genes, particularly the split-cap and rep52 genes, are operably linked to heterologous enhancers.

5. A mammalian cell according to one of the preceding embodiments, wherein at least one of said AAV split-packaging genes is stably integrated into said cell, in one or multiple copies. A preferred embodiment comprises a stably-integrated rep78 gene operably linked to a helper-virus-inducible promoter, and multiple copies of the split-cap and rep52 genes, stably-integrated or transiently introduced.

6. A mammalian cell according to one of the preceding embodiments, wherein at least two different AAV split-packaging genes are stably integrated into said cell, in one or multiple copies.

7. A mammalian cell according to one of the preceding embodiments, wherein at least three different AAV split-packaging genes are stably integrated into said cell, in one or multiple copies.

8. A mammalian cell according to one of the preceding embodiments, further comprising a recombinant AAV vector; preferably, said recombinant AAV vector comprises two AAV inverted terminal repeats and a heterologous gene of interest operably linked to a promoter.

9. A mammalian cell according to embodiment 8, wherein said heterologous gene of interest is a therapeutic gene.

10. A mammalian cell according to embodiment 9, wherein said therapeutic gene encodes a cystic fibrosis transmembrane regulator.

11. A mammalian cell according to one of the preceding embodiments, wherein said mammalian cell is capable of producing at least about 100 recombinant AAV particles per cell. As is described below, virus production is generally initiated by infecting the cells with a helper virus such as adenovirus, or by providing an alternative source of helper virus functions.

12. A mammalian cell according to one of the preceding embodiments, wherein said mammalian cell is capable of producing at least about 200 recombinant AAV particles per cell.

13. A mammalian cell according to one of the preceding embodiments, wherein said cell is capable of producing at least about 400 recombinant AAV particles per cell.

14. A mammalian cell according to one of the preceding embodiments, wherein said mammalian cell is a human cell. In preferred embodiments of the present invention, the cells are capable of producing high titers of heat-stable AAV particles (stable to heating at 56 degrees C. for 30 minutes without substantial loss of infectivity). Also, as discussed in more detail below, preferred split-packaging cells also exhibit a greatly reduced tendency to generate replication-competent AAV ("rcA") particles. In preferred cells, the frequency of generation of rcA is less than about 1 per $10^6$ particles produced, more preferably less that about 1 per $10^8$, still more preferably less than about 1 per $10^{10}$, most preferably less than about 1 per $10^{12}$.

15. A polynucleotide expression vector useful in preparing an AAV split-packaging cell, said expression vector comprising a selectable marker and at least one AAV split-packaging gene selected from the group consisting of:

(i) an AAV split-cap gene, wherein said split-cap gene is uncoupled from Rep78-specific sequences of an AAV rep gene, and wherein said split-cap gene is operably linked to a heterologous promoter, and preferably a heterologous enhancer;

(ii) an AAV rep78 gene, wherein said rep78 gene is uncoupled from Cap-specific sequences of an AAV cap gene, and wherein said rep78 gene is operably linked to a heterologous inducible promoter, preferably a heterologous helper-virus-inducible promoter; and (iii) an AAV rep52 gene, wherein said rep52 gene is uncoupled from Rep78-specific sequences of an AAV rep gene, and wherein said rep52 gene is operably linked to a heterologous promoter, preferably a heterologous helper-virus-inducible promoter.

16. A polynucleotide expression vector according to embodiment 15, comprising an AAV split-cap gene; preferably said gene is operably linked to a heterologous promoter.

17. A polynucleotide expression vector according to embodiment 15, comprising an AAV rep78 gene; preferably said gene is operably linked to a heterologous promoter, more preferably a helper-virus-inducible promoter.

18. A polynucleotide expression vector according to embodiment 15, comprising an AAV rep52 gene; preferably said gene is operably linked to a heterologous promoter.

19. A polynucleotide expression vector according to one of embodiments 15–18, wherein said expression vector comprises the following two AAV split-packaging genes:

(i) an AAV split-cap gene, wherein said split-cap gene is uncoupled from Rep78-specific sequences of an AAV rep gene, and wherein said split-cap gene is operably linked to a heterologous promoter; and (ii) an AAV rep52 gene, wherein said rep52 gene is uncoupled from Rep78-specific sequences of an AAV rep gene, and wherein said rep52 gene is operably linked to a heterologous promoter.

20. A polynucleotide expression vector according to embodiment 19, wherein said AAV split-cap gene and said AAV rep52 gene are arranged in tandem transcriptional orientation.

21. A polynucleotide expression vector according to embodiment 19, wherein said AAV split-cap gene and said AAV rep52 gene are arranged in divergent transcriptional orientation.

22. A method of generating a mammalian cell useful for high efficiency packaging of a recombinant adeno-associated virus (rAAV) vector, comprising introducing into said cell a polynucleotide expression vector according to one of embodiments 15–21.

23. A method of generating a mammalian cell useful for high efficiency packaging of an rAAV vector, comprising introducing into said cell at least two different polynucleotide expression vectors according to one of embodiments 15–21.

24. A method of generating a mammalian cell useful for high efficiency packaging of an rAAV vector, comprising introducing into said cell at least three different polynucleotide expression vectors according to one of embodiments 15–21.

25. A method of generating a mammalian cell useful for high efficiency packaging of an rAAV vector, comprising stably introducing into said cell a polynucleotide expression vector according to one of embodiments 15–21.

26. A method of generating a mammalian cell useful for high efficiency packaging of an rAAV vector, comprising stably introducing into said cell at least two different polynucleotide expression vectors according to one of embodiments 15–21.

27. A method of generating a mammalian cell useful for high efficiency packaging of an rAAV vector, comprising stably introducing into said cell at least three different polynucleotide expression vectors according to one of embodiments 15–21.

28. A mammalian cell generated according to one of embodiments 22–27.

29. A method of generating an infectious replication-incompetent rAAV vector, comprising introducing helper virus functions into a cell of claim 28, and incubating said cell.

DETAILED DESCRIPTION OF THE INVENTION

Figure 1:
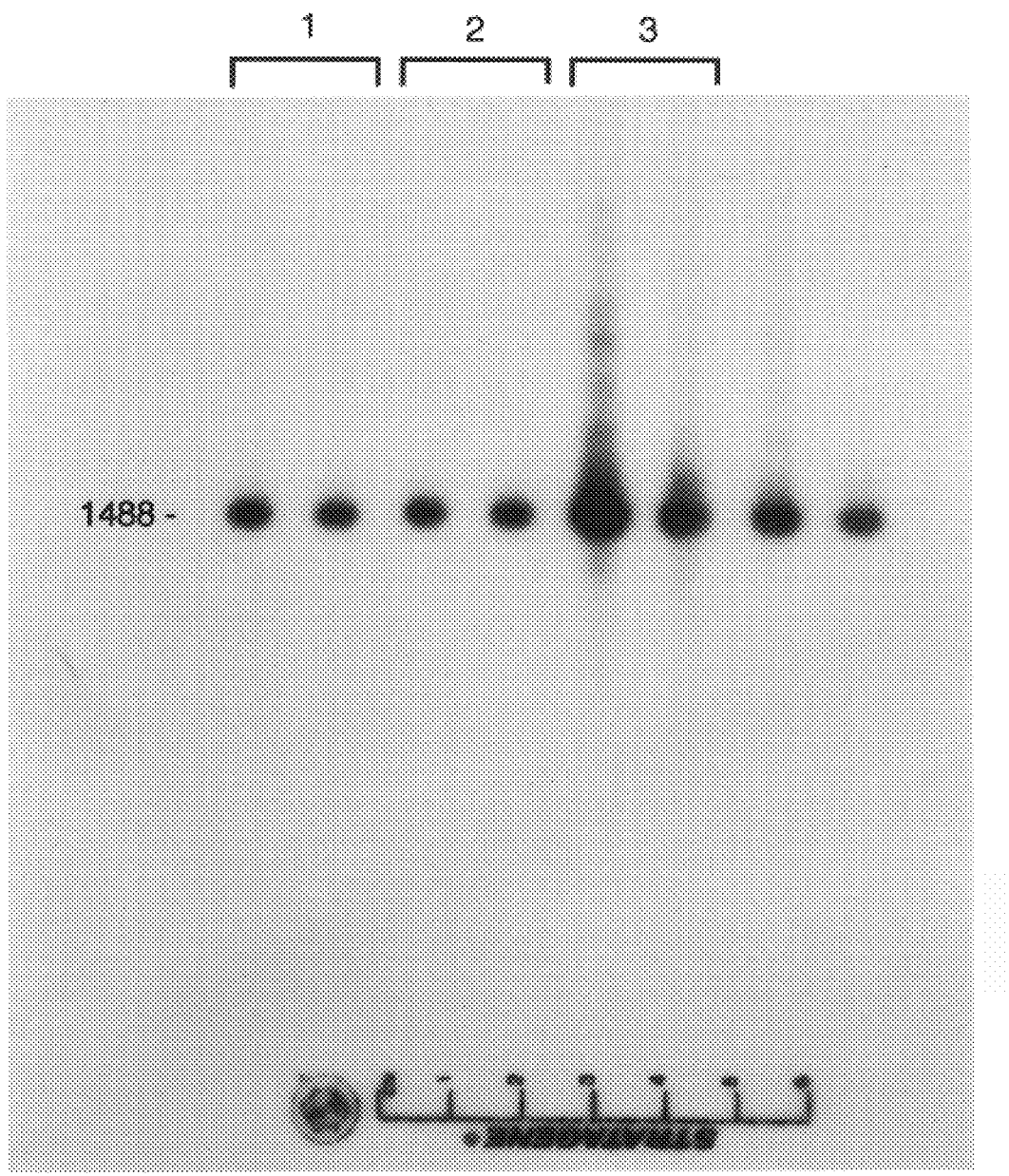
FIG. 1 shows the results of Southern blots indicating that AAV split-packaging genes of the present invention can be used to provide AAV replication and encapsidation functions effective for the production of infectious AAV vector particles useful for delivering a transgene to a target cell, as described in Example 12.

Recombinant AAV vectors are potentially powerful tools for human gene therapy, particularly for diseases such as cystic fibrosis and sickle cell anemia. A major advantage of rAAV vectors over other approaches to gene therapy is that they generally do not require ongoing replication of the target cell in order to become stably integrated into the host cell.

The invention described herein provides methods and materials for use in the production of high titers of recombinant AAV vectors for use in gene therapy.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, *Molecular Cloning: A Laboratory Manual,* Second Edition (1989), *Oligonucleotide Synthesis* (M. J. Gait Ed., 1984), *Animal Cell Culture* (R. I. Freshney, Ed., 1987), the series *Methods in Enzymology* (Academic Press, Inc.); *Gene Transfer Vectors for Mammalian Cells* (J. M. Miller and M. P. Calos eds. 1987), *Handbook of Experimental Immunology,* (D. M. Weir and C. C. Blackwell, Eds.), Current Protocols in Molecular Biology (F. M. Ausubel, R. Brent, R. E. Kingston, D. D. Moore, J. G. Siedman, J. A. Smith, and K. Struhl, eds., 1987), and Current Protocols in Immunology (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

Definition

The terms "polypeptide", "peptide" and "protein" are used interchangeably to refer to polymers of amino acids of any length. These terms also include proteins that are post-translationally modified through reactions that include, but are not limited to, glycosylation, acetylation and phosphorylation.

"Polynucleotide" refers to a polymeric form of nucleotides of any length, either ribonucleotides or deoxyribonucleotides, or analogs thereof. This term refers only to the primary structure of the molecule. Thus, double- and single-stranded DNA, as well as double- and single-stranded RNA are included. It also includes modified polynucleotides such as methylated or capped polynucleotides.

A "gene" refers to a polynucleotide containing at least one open reading frame that is capable of encoding a particular protein after being transcribed and translated.

A "transcriptional regulatory sequence" or "TRS", as used herein, refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Recombinant," refers to a genetic entity distinct from that generally found in nature. As applied to a polynucleotide or gene, this means that the polynucleotide is the product of various combinations of cloning, restriction and/or ligation steps, and other procedures that result in a construct that is distinct from a polynucleotide found in nature.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a TRS (Transcriptional Regulatory Sequence) or promoter that is removed from its native coding sequence and operably linked to a different coding sequence is a heterologous TRS or promoter.

"Sequence overlap" between two polynucleotides occurs when the nucleotides share a homologous sequence. When this homologous sequence is of sufficient length and identity, recombination is facilitated. The level of homology and corresponding frequency of recombination increase with increasing length of the homologous sequences and with their level of shared identity. The level of homology that may pose a concern in a given system can be determined theoretically and confirmed experimentally, as is known in the art. For example, homologous recombination can be substantially reduced or eliminated if the two sequences do not share any stretch of at least 10 base pairs (bp) that is greater than 80% homologous (summed over its length), or any stretch of at least 20 bp that is at least 70% homologous, or any stretch of at least 50 bp that is at least 50% homologous, or any stretch of at least 100 bp that is at least 40% homologous; preferably the levels of homology are even less (preferably less than half of the stated levels), and preferably the lengths of partially homologous sequences are also less (preferably less than half the stated lengths).

A "vector" as used herein refers to a recombinant plasmid or virus that comprises a polynucleotide to be delivered into a host cell, either in vitro or in vivo. The polynucleotide to be delivered, sometimes referred to as a "target polynucleotide" or "transgene", may comprise a coding sequence of interest in gene therapy (such as a gene encoding a protein of therapeutic interest) and/or a selectable or detectable marker.

A "replicon" refers to a polynucleotide comprising an origin of replication which allows for replication of the polynucleotide in an appropriate host cell. Examples of replicons include episomes (including plasmids), as well as chromosomes (such as the nuclear or mitochondrial chromosomes).

"Stable integration" of a polynucleotide into a cell means that the polynucleotide has been integrated into a replicon that tends to be stably maintained in the cell. Although episomes such as plasmids can sometimes be maintained for many generations, genetic material carried episomally is generally more susceptible to loss than chromosomally-integrated material. However, maintenance of a polynucleotide can often be effected by incorporating a selectable marker into or adjacent to a polynucleotide, and then maintaining cells carrying the polynucleotide under selective pressure. In some cases, sequences cannot be effectively maintained stably unless they have become integrated into a chromosome; and, therefore, selection for retention of a sequence comprising a selectable marker can result in the selection of cells in which the marker has become stably-integrated into a chromosome. Antibiotic resistance genes can be conveniently employed in that regard, as is well known in the art. Typically, stably-integrated integrated polynucleotides would be expected to be maintained on average for at least about twenty generations, preferably at least about one hundred generations, still more preferably they would be maintained permanently. The chromatin structure of eukaryotic chromosomes can influence the level of expression of an integrated polynucleotide. Having the genes carried on episomes can be particularly useful where it is desired to have multiple stably-maintained copies of a particular gene. The selection of stable cell lines having properties that are particularly desirable in the context of the present invention are described and illustrated below.

"AAV" is adeno-associated virus. Adeno-associated virus is a defective parvovirus that grows only in cells in which certain functions are provided by a co-infecting helper virus.

General reviews of AAV may be found in, for example, Carter, 1989, *Handbook of Parvoviruses*, Vol. I, pp. 169–228, and Berns, 1990, *Virology*, pp. 1743–1764, Raven Press, (New York). The AAV2 serotype was used in some of the illustrations of the present invention in the Examples. However, it is fully expected that these same principles will be applicable to other AAV serotypes since it is now known that the various serotypes are quite closely related—both functionally and structurally, even at the genetic level (see, e.g., Blacklow, 1988, pp. 165–174 of *Parvoviruses and Human Disease*, J. R. Pattison (ed); and Rose, 1974, *Comprehensive Virology* 3: 1–61). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control.

A "recombinant AAV vector" (or "rAAV vector") refers to a vector comprising one or more polynucleotides of interest (or "transgenes") that are flanked by AAV inverted terminal repeat sequences (ITRs). Such rAAV vectors can be replicated and packaged into infectious viral particles when present in a host cell that has been infected with a suitable helper virus and is expressing AAV rep and cap gene products (i.e. AAV Rep and Cap proteins). When an rAAV vector is incorporated into a larger polynucleotide (e.g. in a chromosome or in another vector such as a plasmid used for cloning or transfection), then the rAAV vector is typically referred to as a "pro-vector" (which can be "rescued" by replication and encapsidation in the presence of AAV packaging functions and necessary helper functions).

A "helper virus" for AAV refers to a virus that allows AAV (which is a "defective" parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Packaging" as used herein refers to a series of subcellular events that results in the assembly and encapsidation of a viral vector, particularly an AAV vector. Thus, when a suitable vector is introduced into a packaging cell line under appropriate conditions, it can be assembled into a viral particle. Functions associated with packaging of viral vectors, particularly AAV vectors, are described herein and in the art.

AAV "rep" and "cap" genes are genes encoding replication and encapsidation proteins, respectively. AAV rep and cap genes have been found in all AAV serotypes examined, and are described herein and in the references cited. In wild-type AAV, the rep and cap genes are generally found adjacent to each other in the viral genome (i.e. they are "coupled" together as adjoining or overlapping transcriptional units), and they are generally conserved among AAV serotypes. AAV rep and cap genes are also individually and collectively referred to herein as "AAV packaging genes." Modified AAV packaging genes (including modified rep genes and modified cap genes) are described below for use in the present invention.

An "AAV split-packaging gene" refers to a recombinant gene encoding one or more AAV packaging proteins (including AAV Rep proteins and/or AAV Cap proteins) wherein the split-packaging gene has been separated from one or more AAV packaging genes to which it is normally linked in the AAV genome. Examples of such AAV split-packaging genes include AAV split-cap genes, AAV rep78 genes and AAV rep52 genes, as described herein. In preferred embodiments of the present invention, one or more AAV split-packaging genes is operably linked to a heterologous promoter, as described below.

An AAV "split-cap" gene refers to a recombinant gene encoding one or more AAV Cap proteins, which gene is separated from Rep78-specific sequences of an AAV rep gene, but is operably linked to a promoter, preferably a heterologous promoter. As described above and in the cited literature, the wild-type AAV rep gene contains two promoter sequences, p5 and p19, which drive expression of the "large Rep proteins" (Rep78 and Rep68) and the "small Rep proteins" (Rep52 and Rep40), respectively; and the wild-type AAV cap gene contains a promoter, p40, which drives expression of the AAV Cap proteins (VP1, VP2 and VP3). AAV cap genes of the present invention (and other AAV packaging genes of the present invention) can also be obtained from non-human adeno-associated viruses, as described in WO 95/20671, published Aug. 3, 1995. In preferred recombinant constructs and cell lines of the present invention, the Cap proteins are encoded by a split-cap gene which, unlike the situation in wild-type AAV, is not located next to a gene capable of encoding the large Rep proteins. Rather, an AAV "rep78" gene (a gene capable of encoding the large Rep proteins Rep78 and Rep68) is provided separately, at a different location. The split-cap genes can be physically separated from Rep78-specific sequences by being present on different replicons or vectors, or, if present on a single replicon or vector, by being separated from Rep78-specific sequences by intervening non-AAV DNA, as described and illustrated in more detail below. In certain preferred embodiments of the present invention, a split-cap gene is operably linked to a heterologous promoter (i.e. a promoter other than the AAV p40 promoter) which heterologous promoter is incorporated upstream of the split-cap coding region, either in place of or in addition to the p40 promoter. Examples of such recombinant split-cap genes operably linked to various promoters, including both inducible and constitutive promoters, are described and illustrated below.

An AAV "rep78" gene is a gene capable of encoding the large Rep proteins Rep78 and Rep68 (and will generally also encode the small Rep proteins Rep52 and Rep40). In certain preferred embodiments of the present invention, a rep78 gene is operably linked to a heterologous promoter (i.e. a promoter other than the AAV p5 promoter) which hleterologous promoter is incorporated upstream of the rep78 coding region, either in place of or in addition to the p5 promoter. Most preferably, the rep78 gene is operably linked to an inducible promoter, most preferably a helper-virus-inducible promoter, as described below.

An AAV "rep52 gene" is capable of separately encoding just the small Rep proteins (i.e. Rep52 and Rep40). In certain preferred embodiments of the present invention, a rep52 gene is operably linked to a heterologous promoter (i.e. a promoter other than the AAV p19 promoter) which heterologous promoter is incorporated upstream of the rep52 coding region, either in place of or in addition to the p19 promoter. An AAV split-cap gene, rep52 gene and/or rep 78 gene can also be operably linked to other transcriptional regulatory sequences, including enhancers and polyadenylation ("polyA") sequences (which additional TRS's can also be heterologous). AAV-derived split-cap genes, rep52 genes and rep78 genes as described herein are collectively referred to as "AAV split-packaging genes." Various examples of the construction and use of such AAV split-packaging genes are described and illustrated below.

A "terminator" refers to a polynucleotide sequence that tends to diminish or prevent read-through transcription (i.e. it diminishes or prevents transcription originating on one side of the terminator from continuing through to the other side of the terminator).

"Efficiency" when used in describing a cell line refers to certain useful attributes of the line; in particular, the growth rate, and (for packaging cell lines) the number of virus particles produced per cell. "High efficiency packaging" indicates production of at least 100 viral particles per cell, more preferably at least about 200 viral particles per cell, still more preferably at least about 400 viral particles per cell. "High safety packaging" indicates that, of the recombinant AAV viral particles produced, fewer than about 1 in $10^6$ are replication-competent AAV viral particles, preferably fewer than about 1 in $10^8$ are replication-competent, more preferably fewer than about 1 in $10^{10}$ are replication-competent, still more preferably fewer than about 1 in $10^{12}$ are replication-competent, most preferably none are replication-competent. Preferred packaging cells of the present invention exhibit combinations of such high efficiency and high safety.

"Host cells", "cell lines", "cell cultures", "packaging cell line" and other such terms denote higher eukaryotic cells, preferably mammalian cells, most preferably human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene", "target polynucleotide", "transgene", "gene of interest" and the like generally refer to a gene or genes to be transferred using a vector. Typically, in the context of the present invention, such genes are located within the rAAV vector (which vector is flanked by inverted terminal repeat (ITR) regions and thus can be replicated and encapsidated into rAAV particles). Target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as E1A tumor suppressor genes or p53 tumor suppressor genes for the treatment of various cancers. To effect expression of the transgene in a recipient host cell, it is generally operably linked to a promoter, either its own or a heterologous promoter. A large number of suitable promoters are known in the art, the choice of which depends on the desired level of expression of the transgene; whether one wants constitutive expression, inducible expression, cell-specific or tissue-specific expression, etc. The rAAV vector may also contain a selectable marker.

Modes of Carrying Out the Invention

The general strategy involves the preparation of mammalian packaging cell lines that comprise various AAV split-packaging genes selected from the following list:

(i) an AAV split-cap gene, wherein said split-cap gene is uncoupled from Rep78-specific sequences of an AAV rep gene, and wherein said split-cap gene is operably linked to a promoter;

(ii) an AAV rep78 gene, wherein said rep78 gene is uncoupled from Cap-specific sequences of an AAV cap gene, and wherein said rep78 gene is operably linked to a promoter; and (iii) an AAV rep52 gene, wherein said rep52 gene is uncoupled from Rep78-specific sequences of an AAV rep gene, and wherein said rep52 gene is operably linked to a promoter.

AAV packaging gene sequences are "uncoupled" as referred to herein when they are located on different replicons or recombinant DNA constructs or, if present on a single replicon or recombinant DNA construct, when they are separated from each other by intervening non-AAV DNA sequences. Preferably, they are separated by at least about 100 nucleotides of other (i.e. non-AAV) DNA, more preferably by at least about 400 nucleotides, more preferably by at least about 1000 nucleotides (1 kb), still more preferably by at least about 2 kb. The term "non-AAV" DNA refers to sequences that do not exhibit any substantial sequence overlap with AAV sequences, as described above. Preferably, such non-AAV DNA would not share any stretch of at least 10 base pairs (bp) that is greater than 80% homologous (summed over its length) with an AAV sequence, or any stretch of at least 20 bp that is at least 70% homologous, or any stretch of at least 50 bp that is at least 50% homologous, or any stretch of at least 100 bp that is at least 40% homologous; preferably the levels of homology are even less (preferably less than half of the stated levels), and preferably the lengths of partially homologous sequences are also less (preferably less than half the stated lengths).

In preferred embodiments of the present invention, split-cap and rep78 genes are introduced separately into the packaging cell line (i.e. they are introduced using separate vectors, and, if stably integrated into the cell, are stably integrated at different locations, i.e. preferably they are separated by other DNA sequence as noted above). A rep52 gene can be introduced separately from a split-cap gene, or they can be introduced together (e.g., on a single recombinant DNA construct). Where they are introduced together, they may be introduced in a common transcriptional orientation (i.e. the promoter driving transcription of the rep52 gene is in the same orientation as the promoter driving transcription of the split-cap gene), or the promoters may be in opposite orientation from each other. Where they are introduced on the same construct, however, they are still preferably separated from each other by non-AAV DNA as described above to reduce the possibility that a replication-competent AAV genome could be regenerated by recombination and also be sufficiently small to be packaged. Examples of such recombinant constructs are described below.

In preferred embodiments of the present invention, one or more different AAV split-packaging genes is stably maintained in the packaging cell line (by integration into a chromosome or a stably-maintained episome); more preferably, at least two different split-packaging genes are stably maintained in the packaging cell line; most preferably three different split-packaging genes are stably maintained in the packaging cell line. Such stable maintenance can be mediated by integration of the split-packaging gene(s) into one or more stably-maintained episomes or into a chromosome of the cell. A split-cap gene and a rep78 gene are preferably maintained on different replicons or, if both are chromosomally integrated, they are preferably introduced separately into the packaging cell line such that they are likely to become integrated at separate sites in the genome. Confirmation that split-packaging genes have become integrated at separate sites can be obtained using routine molecular biological techniques (such as Southern blotting with probes directed to each of the separate genes).

As noted above, preferred embodiments of the present invention will also comprise a rep52 gene. Preferably, such a rep52 gene will also be stably maintained in the packaging cell. The rep52 gene will preferably be introduced separately from the rep78 gene but may be introduced together with (or separately from) the split-cap gene, as discussed above.

The closely-coupled and tightly-regulated rep and cap functions characteristic of wild-type AAV, and various prior packaging systems, are thus uncoupled and substantially reorganized in the packaging cell lines of the present invention. The inventors have found that their redesigned system is capable of providing significantly greater quantities of heat-stable recombinant AAV vectors, while at the same time greatly reducing the possibility of generating replication-competent AAV particles—thus achieving both of the elusive goals of AAV packaging systems referred to above.

Mammalian cells of the present invention can be infected or transfected with a "recombinant AAV vector" (or "rAAV vector") comprising, for example, AAV ITR regions and a heterologous polynucleotide of interest. Under suitable conditions (including suitable growth conditions and infection with a competent helper virus), expression of the rep and cap genes of the packaging cell results in the synthesis of Rep and Cap proteins which mediate replication and encapsidation of the AAV vector, respectively. Providing a polynucleotide of interest (also referred to as a "target polynucleotide") in-between the AAV ITR sequences of the rAAV vector, thus results in packaging of the target polynucleotide into an infectious rAAV particle which can be used to deliver the polynucleotide to a desired host cell. Recent evidence suggests that providing a single ITR can be sufficient to carry out the functions normally associated with two wild-type ITRs (see, e.g., Samulski, R. J. et al., WO 94/13788, published Jun. 23, 1994).

By minimizing the extent of sequence overlap between any AAV genes in the packaging cell line and any sequences of the rAAV vector, the proportion of wild-type AAV particles not containing the target polynucleotide can be minimized. Thus, the rAAV vector will preferably comprise at least one, more preferably two, AAV ITR regions, but will preferably not share any significant sequence overlap with the AAV rep or cap genes (considered in view of the likelihood of avoiding homologous recombination events as discussed above). As described in the Background section, the presence of contaminating replication-competent AAV limits the therapeutic potential of rAAV vector preparations. Besides the lack of any significant sequence overlap in the various recombinant constructs of the present invention, the AAV split-cap and rep78 genes of the present invention are uncoupled from each other, thereby substantially eliminating the possibility that a replication-competent AAV particle could be reconstituted by even non-homologous recombination events. The packaging cell lines of the present invention enable the efficient production of rAAV preparations that are of high titer and are substantially free of any contaminating replication-competent AAV; attributes that are especially useful in the context of AAV-mediated gene therapy.

A first illustration of the principles of the present invention was performed using the AAV2 serotype. However, it is fully expected that these same principles will be applicable to other AAV serotypes since it is now known that the various serotypes are quite closely related—both functionally and structurally, even at the genetic level (see, e.g., Blacklow, 1988, pp. 165–174 of "Parvoviruses and Human Disease", J. R. Pattison (ed); and Rose, 1974, Comprehensive Virology 3:1–61). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control.

Producing the Packaging Cell Line

The parental lines from which packaging cells are generated may be obtained from any cell line that is susceptible to AAV infection, and amenable to culture in vitro. As indicated earlier, AAV has a very broad host range and has been isolated from a variety of mammalian cell types, including simian, human and rodent cells. Such human cell lines from which the packaging cell lines may be derived, include, for example, Hela, A549, 293, KB, Detroit, and WI38 cells. We initially selected various derivatives of human 293 and Hela cells for demonstrations of the present invention In the case of wild-type AAV (using AAV2 for purposes of illustration), the rep gene is under regulation of the p5 promoter, which is itself strongly down-regulated by rep expression. In constructing packaging cell lines according to the present invention, the cells are provided with various AAV split-packaging genes, each operably linked to a promoter. In preferred embodiments, as noted above, one or more of the split-packaging genes is operably linked to a heterologous promoter. Any heterologous promoter that is not strongly down-regulated by rep gene expression is suitable.

For the rep78 gene, inducible promoters are preferred because constitutive expression of the rep78 gene can have a negative impact on the host cell. Presently, the most preferred inducible promoters for the rep78 are those from which little if any transcription occurs in the absence of induction (i.e. inducible promoters known or determined to be tightly "off" in the absence of induction). A variety of such promoters are known in the art or can be readily identified using various promoter-less "reporter" genes. For the split-cap gene and the rep52 gene, preferred heterologous promoters include both constitutive and inducible promoters. Since, in preferred embodiments, the various rep and/or cap genes of the present invention may be stably integrated into the host cell genome, location effects (such as those due to chromatin structure) can also influence expression of the genes and can be taken advantage of in obtaining preferred packaging lines. In particular, the methodology described below can be used to generate and select packaging cells that exhibit the desired properties. Numerous constitutive promoters are known in the art and generally available; including not only mammalian promoters but numerous promoters of viruses found to infect mammals (such as the commonly-used CMV promoter illustrated below). A large variety of inducible promoters are also well known in the art and generally available; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. The cloning of various promoters and confirmation that promoters exhibit the desired levels of expression can be achieved using standard molecular biological techniques as illustrated below and in the references cited herein.

An especially preferred sub-class of inducible promoters are those that are induced by the helper virus that is used to complement the replication and packaging of the rAAV vector. A number of helper-virus-inducible promoters are known, including for example, the adenovirus early gene promoter which is inducible by adenovirus E IA protein; the adenovirus major late promoter; the herpesvirus promoter which is inducible by herpesvirus proteins such as VP16 or 1CP4; as well as vaccinia or poxvirus inducible promoters. International application WO 96/17947 (published Jun. 13, 1996), by J. Allen and Targeted Genetics Corporation, describes helper-virus-inducible promoters and illustrates a generally applicable method that can be used to test putative promoters to readily determine whether or not they are helper-virus-inducible and whether or not they will be useful in the generation of high efficiency packaging cells. Briefly, the method involves replacing, e.g., the p5 promoter of the AAV rep78 gene with a putative helper-virus-inducible promoter (either known in the art or identified using well-known techniques such as linkage to promoter-less "reporter" genes). For example, the AAV rep78 gene (preferably with p5 replaced and preferably linked to a positive selectable marker such as an antibiotic resistance gene), can then be stably integrated into a suitable host cell (such as the derivatives of human 293 and Hela cells exemplified below). Cells that are able to grow relatively well under selection conditions (e.g. in the presence of the antibiotic) are then tested for their ability to express the rep78 gene upon addition of a helper virus.

As an initial test for the expression of various rep and/or cap genes, cells can be readily screened using immunofluorescence to detect Rep and/or Cap proteins (as in the cited art above). Confirmation of packaging capabilities and efficiencies can also be obtained by functional tests for replication and packaging of incoming rAAV vectors (as illustrated below). Using these methodologies, for example, we constructed a rep78 gene in which the p5 promoter was replaced with a heterologous promoter, constructed a split-cap gene in which the p40 promoter was replaced with a different heterologous promoter, constructed a rep52 gene in which the p19 promoter was replaced with a different heterologous promoter, and used the resulting constructs to generate split packaging cell lines capable of producing high titers of rAAV particles with little or no possibility of generating replication-competent AAV particles.

In particular illustrative examples below, we prepared a variety of plasmids encoding various AAV split-packaging genes according to the present invention. For example, as an illustration of the construction of a split-cap gene, we prepared a plasmid called "CMV-cap" comprising a heterologous constitutive promoter (from CMV), operably linked to AAV cap sequences, followed by a heterologous polyA signal (from SV40). Other exemplary constructs comprising split-cap genes operably linked to inducible promoters are also described. As an illustration of the construction of a rep78 gene, we prepared a plasmid called "mMT1-rep78" comprising a heterologous inducible promoter (from the mouse metallothionein I regulatory region), operably linked to AAV rep sequences, followed by a heterologous polyA signal (from the mouse metallothionein I gene). As an illustration of the construction of a rep52 gene, we prepared a plasmid called "mMT1-rep52" comprising a heterologous inducible promoter (from the mouse metallothionein I regulatory region), operably linked to AAV rep52 sequences, followed by a heterologous polyA signal (from the mouse metallothionein I gene). We also constructed illustrative expression plasmids comprising both split-cap and rep52 genes, both in tandem and opposing orientations.

AAV split-packaging cells prepared as described herein have been used to effectively replicate and encapsidate an illustrative recombinant AAV vector comprising a therapeutically beneficial gene (encoding a cystic fibrosis transmembrane conductance regulator or "CFTR"); and rAAV virus particles prepared using split-packaging genes according to the present invention have been used to efficiently infect human cells, thereby enabling the introduction of such a therapeutic gene into such cells.

Cells transfected with AAV split-packaging genes as described above can be selected from untransfected cells according to methods that are routine in the art. Most conveniently, selection can be accomplished by linking the split-packaging genes to one or more selectable markers (such as antibiotic resistance genes). Preferably, such selectable markers are driven by constitutive promoters; and preferably, such markers are introduced in an opposite orientation relative to the AAV split-packaging genes, especially rep genes, since that tends to reduce the potential for the promoter driving the selectable marker to also cause expression of the rep gene (which can be detrimental to the host cell). After transfection and recovery, the cell lines are exposed to the antibiotic for which resistance has been provided (as illustrated below).

Integration of a gene into a host cell can be conveniently monitored using Southern analysis, for example. Expression of Rep and/or Cap proteins can also be assayed using any of a variety of techniques; including structural assays (such as immunofluorescence), and functional assays (such as replication and packaging of an integrated or incoming rAAV vector, as described in the Examples below).

The preferred packaging cells of the present invention are capable of replicating at least one half as rapidly as the parental cells from which they were derived, more preferably at least two-thirds as rapidly, still more preferably at least 90% as rapidly. Preferred packaging cells according to the present invention are also capable of producing at least about 100 rAAV particles/cell, more preferably at least about 200 rAAV particles/cell, still more preferably at least about 400 rAAV particles/cell.

Generating rAAV Vectors

To generate recombinant AAV particles useful for such purposes as gene therapy, the packaging cell line is preferably supplied with a recombinant AAV vector comprising AAV inverted terminal repeat (ITR) regions surrounding one or more polynucleotides of interest (or "target" polynucleotides).

The target polynucleotide is generally operably linked to a promoter, either its own or a heterologous promoter. A large number of suitable promoters are known in the art, the choice of which depends on the desired level of expression of the target polynucleotide (i.e. whether one wants constitutive expression, inducible expression, cell-specific or tissue-specific expression, etc.).

By way of illustration, we have used rAAV vectors containing polynucleotides that encode a functional cystic fibrosis transmembrane conductance regulator polypeptide (CFTR) operably linked to a promoter. As is now known in the art, there are a variety of CFTR polypeptides that are capable of reconstructing CFTR functional deficiencies in cells derived from cystic fibrosis patients. For example, Rich et al. (1991, Science, 253:205–207) described a CFTR derivative missing amino acid residues 708–835, that was capable of transporting chloride and capable of correcting a naturally occurring CFTR defect. Egan et al. (1993) described another CFTR derivative (comprising about 25 amino acids from an unrelated protein followed by the sequence of native CFTR beginning at residue 119) that was also capable of restoring electrophysiological characteristics of normal CFTR. To take two additional examples, Arispe et al. (1992, Proc. Natl. Acad. Sci. USA 89: 1539–1543) showed that a CFTR fragment comprising residues 433–586 was sufficient to reconstitute a correct chloride channel in lipid bilayers; and Sheppard et al. (1994, Cell 76:1091–1098) showed that a CFTR polypeptide truncated at residue 836 to about half its length was still capable of building a regulated chloride channel. Thus, the native CFTR protein, and mutants and fragments thereof, all constitute CFTR polypeptides that are useful under this invention.

Other useful target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as the wild-type p53 tumor suppressor cDNA for replacement of the missing or damaged p53 gene associated with some lung and breast cancers, or the E1A tumor suppressor gene which is capable of inhibiting tumorigenesis and/or metastasis of a variety of different cancers including breast and ovarian cancers.

Since the therapeutic specificity of the resulting recombinant AAV particle is determined by the particular vector or pro-vector introduced, the same basic packaging cell line can be modified for any of these applications. For example, a vector comprising a specific target polynucleotide can be introduced into the packaging cell for production of the AAV vector by any of several possible methods; including, for example, electroporation or transfection of a plasmid comprising an rAAV pro-vector, or infection with an rAAV or helper virus comprising an rAAV vector or pro-vector.

Helper virus can be introduced before, during or after introduction of the rAAV vector. For example, the plasmid can be co-infected into the culture along with the helper virus; and the cells can then be cultured for a sufficient period, typically 2–5 days, in conditions suitable for replication and packaging as known in the art (see references above and examples below). Lysates are prepared, and the recombinant AAV vector particles are purified by techniques known in the art.

In a preferred embodiment, also illustrated in the Examples below, a recombinant AAV vector is itself stably integrated into a mammalian cell to be used for packaging. Such rAAV "producer cells" can then be grown and stored until ready for use. To induce production of rAAV particles from such producer cells, the user need only infect the cells with helper virus and culture the cells under conditions suitable for replication and packaging of AAV (as described below).

Alternatively, one or more of the AAV split-packaging genes or the rAAV vector can be introduced as part of a recombinant helper virus. For example, the E1, E3 and/or the E4 genes of adenovirus can be replaced with one or more split-packaging genes or an rAAV vector. Techniques for facilitating cloning into adenovirus vectors, e.g. into the E1 and/or E3 regions, are known in the art (see, e.g., Bett, A. J., et al., Proc. Natl. Acad. Sci. USA 91:8802–8806, 1994). Thus, a helper virus such as a recombinant adenovirus, can be used to provide helper virus functions as well as AAV packaging genes and/or an rAAV pro-vector, since (as is known in the art) a number of genes in such a helper virus (e.g. the E3 gene of adenovirus) can be replaced without eliminating helper virus activity. Additional genes can be inserted into such a helper virus by providing any necessary helper virus functions in trans. For example, human 293 cells contain adenoviral genes that can complement adenoviral E1 mutants. Thus, heterologous genes can also be cloned into an adenovirus in which the E1 genes have been deleted, for use in cells that can effectively provide such adenoviral functions in trans. Alternatively, the use of a helper virus can be eliminated by providing all necessary helper virus functions in the packaging cell.

The examples presented below are provided as a further guide to the practitioner of ordinary skill in the art, and are not to be construed as limiting the invention in any way.

EXAMPLES

Example 1
Illustrative Construction of a Split-cap Gene

As an initial illustration of the generation of a split-cap gene, a plasmid called "CMV-cap" was constructed comprising a heterologous constitutive promoter operably linked to AAV cap sequences, followed by a heterologous polyadenylation (polyA) signal.

Essentially, CMV-cap was constructed using standard molecular biological techniques (as described, e.g., in Ausubel et al., Current Protocols in Molecular Biology, Greene Publishing Assoc., New York, 1987 and updates) to comprise the following component sections:

(i) a HindIII to BglII fragment containing nucleotides 1881–4496 encoding the capsid gene from the pAV2 plasmid (Laughlin, C. A., et al., Gene 23:65–73 (1983)); which (after partially filling in the HindIII site to generate a unique NheI site) was cloned into the following fragment, (ii) the NheI to BglII backbone of plasmid "tgCMV-HyTK" (Lupton, S. D., et al., Molecular and Cellular Biology 11:3374–3378 (1991)).

The plasmid tgCMV-HyTK backbone consists of the following four components:

(i) the BaI-SstII fragment containing the HCMV IE94 promoter (Boshart, M. F., et al., Cell 41:521–530 (1985));

(ii) nucleotides 1881–4496 from the pAV2 plasmid (Laughlin, C. A., et al., Gene 23:65–73 (1983)) encoding the cap gene;

(iii) the BcI-BamHI fragment from the simian virus 40 genome containing the SV40 early region poly A region (Tooze, J. (ed.), Molecular Biology of Tumor Viruses, DNA tumor viruses (2nd ed.). Cold Spring Harbor Laboratory, Cold Spring Harbor, N.Y. (1981)); and (iv) the NruI-A1wN1 fragment from pML2d (Lusky, M. and M. Botchan, Nature 293:79–81 (1981)) containing the bacterial replication origin and the A1wN1-AatII fragment from pGEM1 (Promega Corp.) containing the β-lactamase gene (which provides ampicillin resistance to facilitate the cloning process).

Example 2
Illustrative Construction of a Rep78 Gene

As an illustration of the construction of a rep78 gene, we prepared a plasmid (called "mMT1-rep78") comprising a heterologous inducible promoter operably linked to AAV rep sequences, followed by a heterologous polyA signal.

Essentially, mMT1-rep78 was constructed using standard molecular biological techniques (as described, e.g., in Ausubel et al., Current Protocols in Molecular Biology, Greene Publishing Assoc., New York, 1987 and updates) to comprise the following four component sections:

i) vector backbone: pBluescript KS(+)(available from Stratagene), into which had been inserted a neomycin resistance gene (under the control of an SV40 promoter and followed by an SV40 polyA sequence (as described for pMT-rep/cap//pKO-neo in WO 96/17947, by James M. Allen and Targeted Genetics Corporation, published Jun. 13, 1996) to facilitate selection in both bacterial cells (using neomycin) and in mammalian cells (using G418);

ii) mMT1: mouse metallothionein I regulatory region on a KpnI/BglII fragment (KpnI is at −589 according to Bacolla, A. et al., Nucleic Acids Res. 19:1639–1647, 1991; BglII is +64 according to Glanville et al., Nature 292:267–269, 1981);

iii) rep78: AAV rep sequences from 311 to 2188 (sequence according to Srivastava et al., J. Virol. 45:555–564, 1983) followed by the sequence 5'-CTAGA CCTCC TCAGA TTAGC GAGGG GCCAT AGCTT ATGAG CTAGC CGC-3' (SEQ ID NO: 1) to provide the spliced second rep exon; and iv) poly A$^+$ signal: from the mouse metallothionein I gene on an SstII/HindIII fragment (SstII is at 925 and HindIII is at 1246 according to Glanville et al., Nature 292:267–269, 1981).

Example 3
Illustrative Construction of a Rep52 Gene

As an illustration of the construction of a rep52 gene, we prepared a plasmid (called "mMT1-rep52") comprising a heterologous inducible promoter operably linked to AAV rep52 sequences, followed by a heterologous polyA signal.

Essentially, mMT1-rep52 was constructed using standard molecular biological techniques (as described, e.g., in Ausubel et al., Current Protocols in Molecular Biology, Greene Publishing Assoc., New York, 1987 and updates) to comprise the following four component sections:

i) vector backbone: pBluescript KS(+)(available from Stratagene) into which had been inserted an L-histidinol resistance gene (HisD$^R$) gene (as described in Hartmann, S. C., et al., Proc. Nat'l. Acad. Sci. USA 85:8047–8051, and including the SV40 polyA signal);

ii) mMT1: mouse metallothionein I regulatory region on a KpnI/BglII fragment (KpnI is at −589 according to Bacolla, A. et al., Nucleic Acids Res. 19:1639–1647, 1991; BglII is +64 according to Glanville et al., Nature 292:267–269, 1981);

iii) rep52: AAV rep sequences from 964 to 2188 (sequence according to Srivastava et al., J. Virol. 45:555–564, 1983) followed by the sequence 5'-CTAGA CCTCC TCAGA TTAGC GAGGG GCCAT AGCTT ATGAG CTAGC CGC-3' (SEQ ID NO: 1) to provide the spliced second rep exon; and iv) poly A$^+$ signal: from the mouse metallothionein I gene on a SstII/HindIII fragment (SstII is at 925 and HindIII is at 1246 according to Glanville et al., *Nature* 292:267–269, 1981).

Example 4

Illustrative Construction of a First Expression Plasmid Comprising a Split-cap Gene and a Rep52 Gene(Tandem Orientation)

As a first illustration of the construction of an expression plasmid comprising a split-cap gene and a rep52 gene, we prepared a plasmid (called "CMV-cap/mMT1 -rep52/ (tandem orientation)") comprising a heterologous constitutive promoter operably linked to AAV cap sequences, and a heterologous inducible promoter operably linked to AAV rep52 sequences, each incorporated into the plasmid in the same transcriptional orientation.

Essentially, CMV-cap/mMT1-rep52/(tandem orientation) was constructed using standard molecular biological techniques (as described, e.g., in Ausubel et al., *Current Protocols in Molecular Biology*, Greene Publishing Assoc., New York, 1987 and updates) to comprise the following three component sections:

i) vector backbone: pBluescript KS(+)(as above);

ii) a CMV-split-cap gene (constructed as described above in Example 1), inserted into an mMT1-rep52 vector (as described above in Example 3), by insertion at a NotI site in the polylinker 5' of the mMT1 regulatory region such that the CMV promoter is oriented in the same direction as the mMT1 promoter; and iii) mMT1-rep52: as described above in Example 3.

Example 5

Illustrative Construction of a Second Expression Plasmid Comprising a Split-cap Gene and a Rep52 Gene (Divergent Orientation)

As a second illustration of the construction of an expression plasmid comprising a split-cap gene and a rep52 gene, we prepared a plasmid (called "CMV-cap/mMT1-rep52/ (divergent orientation)") comprising a heterologous constitutive promoter operably linked to AAV cap sequences, and a heterologous inducible promoter operably linked to AAV rep52 sequences, incorporated into the plasmid in opposing transcriptional orientations.

Essentially, CMV-cap/mMT1-rep52/divergent orientation was constructed using standard molecular biological techniques (as described, e.g., in Ausubel et al., *Current Protocols in Molecular Biology*, Greene Publishing Assoc., New York, 1987 and updates) to comprise the following three component sections:

i) vector backbone: pBluescript KS(+)(as above);

ii) a CMV-split-cap gene (constructed as described above in Example 1), inserted into an mMT1-rep52 vector (as described above in Example 3), by insertion at a NotI site in the polylinker 5' of the mMT1 regulatory region such that the CMV promoter is oriented in the opposite direction as the mMT1promoter; and iii) mMT1-rep52: as described above in Example 3.

Example 6

Illustrative Construction of a Recombinant AAV Vector

An illustrative example of a recombinant AAV vector containing a gene of interest is an rAAV vector containing a gene encoding a cystic fibrosis transmembrane conductance regulator (CFTR), such as the vector pTRF42 described by Flotte et al. (1993), *J. Biol. Chem.* 268:3781–3790. The pTRF42 construct is an AAV-CFTR vector comprising 145 nucleotides of the AAV 5' end (the ITR) followed by an in-frame ATG (Met) initiation codon, reading directly into the CFTR coding sequence from amino acid 1119. The remainder of the CFTR cDNA is intact (including the native termination codon and up to nucleotide 4629 of the original sequence). This sequence is followed by a synthetic polyadenylation signal, and then by AAV nucleotides 4490–4681 (3' ITR); as described by Flotte et al., supra, (see also the vector described by Riordan et al. (1989) *Science* 245:1066–1073).

Another rAAV vector containing a CFTR, termed tgAAVCFTR, contains the AAV2 inverted terminal repeats (nucleotides 1–145 and 4490–4681) flanking nucleotides 133 to 4573 of the CFTR cDNA (entire coding sequence) and a synthetic polyadenylation signal based on the murine beta-globin at the 3' end, see, Afione, S. A., et al., *J. Virol.* 70:3235–3241, 1996)). This rAAV vector was used to generate cell lines comprising stably-integrated rAAV vectors, as described below.

It is also convenient, for assaying packaging cell functions, to employ an rAAV test vector comprising a selectable or detectable marker gene as has been described in the art (see, e.g., the descriptions of rAAV vectors comprising the selectable marker gene neo and vectors comprising the detectable gene lacZ in WO 95/13365, by T. Flotte et al., Targeted Genetics Corporation and Johns Hopkins University, published May 18, 1995).

Example 7

Illustrative Construction of a Cell Line with a Stably Integrated AAV Vector

A variety of different mammalian cell lines comprising stably-integrated rAAV pro-vectors have been generated. By way of illustration, an rAAV pro-vector was stably integrated into 293 cells (ATCC CRL 1573). Briefly, this line, referred to as 293/AAVCFTR herein, was generated by electroporating 293 cells with plasmid "tgAAVCFTR" as described above.

Selection for clones that had incorporated a copy of the rAAV (comprising CFTR) was performed on medium containing 750 micrograms/ml hygromycin. Confirmation that a clonal line contained an integrated full-length copy of the rAAV pro-vector was accomplished by performing Southern blotting of RI-digested genomic DNA and probing blots with a CFTR-specific probe.

Human cells such as 293 cells and various derivatives of such cells were generally maintained in Dulbecco's modified Eagle's Medium (DMEM) supplemented with 10% calf serum and 100 units/ml penicillin and streptomycin. Cells were grown in a humidified 37 degree C incubator supplemented with 10% $CO_2$.

Generally, electroporation of such cells was performed using 15–30 micrograms of plasmid DNA for 2–5×10$^6$ cells, and was routinely performed in about 800 microliters of serum-free medium in a 0.4 cm cuvette at 210 volts, 960 microF using a Gene Pulser (Bio-Rad). After electroporation, cells were typically plated in a T-75 flask in DMEM comprising a selective component (e.g., 0.65–1.2 mg/ml G418 (Gibco-BRL) for cells having a neomycin resistance gene such as a neo or geo gene). The selected cell population was expanded and maintained in selective medium.

Example 8
Illustrative Construction of a Second Cell Line with a Stably Integrated AAV Vector In addition to the cells described above, we also prepared other mammalian cell lines including Hela S3 cells (which are a suspension-adaptable human Hela cell line (ATCC CCL 2.2)), that comprise stably-integrated rAAV vectors (AAVCFTR); and have introduced AAV split-packaging genes into such cells. Briefly, an rAAV pro-vector (comprising an ITR-flanked CFTR gene in a plasmid backbone comprising a hygromycin resistance gene under control of the CMV promoter), was electroporated into Hela S3 cells, essentially as described above and in the art. Selection for clones that had incorporated a copy of the rAAV pro-vector (comprising CFTR) was performed on medium containing 750 micrograms/ml hygromycin. Confirmation that a clonal line contained an integrated full-length copy of the rAAV pro-vector was accomplished by performing Southern blotting of RI-digested genomic DNA and probing blots with a CFTR-specific probe. The resulting clonal lines are referred to as HelaS3/AAVCFTR.

Example 9
Illustrative of an AAV Titering Assay

A variety of assays for titering recombinant AAV vectors have been described in the art. For the following examples, we used an AAV titering assay employing Hela clone 37 cells (with an integrated copy of mMT1rep-cap, a rep-cap cassette in which the rep gene was placed under the control of the mouse metallothionein promoter as described in WO 96/17947, by James M. Allen and Targeted Genetics Corporation, published Jun. 13, 1996). Briefly, in that published application, rep activity assays were performed in order to determine whether there was a linear relationship between incoming AAVCFTR virus and replicated AAVCFTR sequences (which could be exploited as the basis of an rAAV infectious titer assay). Three log dilutions from $1.2 \times 10^9$ to $1.2 \times 10^7$ AAVCFTR particles, as determined by slot blot hybridization, were cultured in 2.5 ml media on $2.5 \times 10^5$ Hela clone 37 cells plus adenovirus (MOI=25 pfu/cell) for 48 hours in a 6 well culture dish. As a negative control, $1.2 \times 10^9$ AAVCFTR particles minus adenovirus was included. After 48 hours, total nucleic acid was prepared from the cells for Southern analysis to detect replicated CFTR sequences.

Those results demonstrated that the clone 37 cells are capable of effectively replicating an incoming rAAV vector in the presence of adenovirus, and that this activity can be used to quantify the number of infectious viral particles present in a given sample. This "clone 37 assay" for infectious virus titer can thus be used to conveniently monitor the infectious titer of various AAV virus lysates, as illustrated below.

Example 10
Illustrative Transfection Protocol

As is well known in the art, there are a wide variety of well-known procedures for introducing polynucleotides into mammalian cells (see, e.g., the references cited above).

To introduce polynucleotides stably into recipient mammalian cells, we generally used an electroporation procedure to introduce plasmid DNAs and selected for stable integrants as described above.

To introduce polynucleotides transiently, e.g. in conjunction with infection by adenovirus, we generally used a lipofection procedure. In general, we transfected mammalian cells using Gibco BRL's Lipofectamine™ reagents following the recommended procedures. This procedure can be employed, for example, in introducing various AAV packaging gene constructs into cells (such as cells comprising an integrated rAAV pro-vector (such as 293/AAVCFTR and HelaS3/AAVCFTR as described above) in order to assess the ability of the constructs to mediate rescue and amplification of the rAAV pro-vector (which requires AAV Rep protein functions as well as helper virus, such as adenovirus). In addition, where AAV cap genes are also provided, the rescued amplified AAV pro-vector can also be packaged into infectious AAV vector particles, which can be tested in an infectious AAV titer assay using Hela clone 37 cells, as described above.

Transfections using lipofectamine were performed according to standard procedures. Briefly, target cells were seeded at about $1.5 \times 10^6$ cells in a T75 flask (at about 60%–70% confluency) using M/02 medium (Minimum Essential Medium (MEM) supplemented with 10% fetal bovine serum and 2 mM L-glutamine). Prior to addition of the DNA/lipofectamine complex the cells were incubated with adenovirus (at an MOI of 5) for 1 hr. The DNA/lipofectamine complex was prepared at a DNA/lipofectamine ratio of about 1:2 ($\mu g : \mu l$), using about 10–30 micrograms of plasmid DNA per T75 flask, in a final volume of 7 ml. Following a change to serum-free media in the cell flasks, DNA/lipofectamine complex was added to each flask and the flasks were then incubated for about 4 hrs @37° C. At 4 hrs the transfection media was replaced with complete medium, and the cells were allowed to incubate for 48–72 hours, after which cells were harvested.

Cells containing an rAAV pro-vector that have been infected with adenovirus and have AAV packaging genes (i.e. AAV rep and/or cap genes, either transiently introduced or stably integrated) can, after incubation, be examined for rAAV rescue and amplification and/or production of infectious AAV vector particles. Such cells can be conveniently divided into fractions for subsequent analysis. For example, one fraction can be used to examine rAAV rescue and amplification (by isolating and purifying DNA, digesting the DNA with a restriction enzyme such as EcoRI, running the DNA on a gel and transferring to a blot for hybridization such as by the Southern procedure, and then probing the blot with a radioactive probe specific for the rAAV vector, such as a probe specific for a 1.488 kb EcoRI fragment from the CFTR gene). Another fraction can be used to monitor the production of infectious viral particles (by obtaining viral lysates). Typically, viral lysates were obtained by resuspending cells in 10 mM Tris buffer, and sonicating the cells (generally in 15 second intervals for a period of about 2 minutes).

Example 11
Introduction of AAV Split-packaging Genes into Human 293 Cells Comprising Stably-Integrated recombinant AAV Pro-vectors Following essentially the same procedures as described above, we introduced various AAV packaging genes into a clone of 293 cells ("clone 21") that had a stably-integrated rAAV pro-vector (293/AAVCFTR cells as described above).

In this example, we examined the effect of introducing AAV split-packaging genes (in particular, a rep52 gene and a split-cap gene) into cells along with a plasmid (mMT1-rep-cap) that carried both an AAV rep gene and an AAV cap gene. The "positive control" was a plasmid ("pRS5") which contains the AAV rep and cap genes in which the rep gene is placed under the control of the HIV LTR promoter (as described in WO 95/13365, by T. Flotte et al., Targeted Genetics Corporation and Johns Hopkins University, published May 18, 1995). The plasmids (10 micrograms each)

were introduced by lipofection, after adenovirus infection, as described above, in the following combinations: (i) pRS5; (ii) mMT1-rep-cap; and (iii) mMT1-rep-cap plus the split-packaging plasmids mMT1-rep52 and CMV-cap. After a 72 hour incubation, cells were harvested, resuspended in 500 microliters of 10 mM Tris buffer, and then sonicated in 15 second intervals for a period of 2 minutes. A portion of the crude lysate was then heated at either 56 degrees Celsius (or simply incubated at 37 degrees Celsius) for 30 minutes. Lysates (50 microliters) were then assayed for the ability to infect a host cell (in the clone 37 assay as described above). (Since heat treatment inactivates adenovirus, an aliquot of adenovirus was added back to one of the heat-treated samples prior to conducting the clone 37 assay (thus, each lysate was sub-divided into three portions, one of them unheated, one of them heated and supplemented with adenovirus, and the last heated but not supplemented with adenovirus).

The results demonstrated that "super-transfection" with the AAV split-packaging genes resulted in a substantial increase (approximately 10- to 20-fold) in the production of infectious rAAV virus particles as measured in the clone 37 assay; and further revealed that the super-transfection with the split-packaging genes resulted in the generation of heat-stable rAAV virus particles which, with additional adenovirus, could infect clone 37 cells essentially as well as the unheated lysate.

Example 12
Ability of a Cell Line Comprising Only AAV Split-packaging Genes to Mediate Rescue and Amplicication of an Integrated Recombinant AAV Pro-vector and to Generate Heat-stable Infectious Vector Particles Following essentially the same procedures as described above, we introduced various AAV split-packaging constructs into cells carrying an integrated rAAV vector. In this example, we examined the effect of introducing AAV split-packaging genes (in particular, a rep78 gene and a split-cap gene) into 293/AAVCFTR cells. The positive controls were plasmids comprising complete rep-cap cassettes (pRS5 and mMT1-rep-cap as described above). The plasmids (10 micrograms each) were introduced by lipofection, after adenovirus infection, as described above, in the following combinations: (i) pRS5; (ii) mMT1-rep-cap; and (iii) split-packaging plasmids mMT1-rep78 and CMV-cap. After a 72 hour incubation, cells were harvested, resuspended in 500 microliters of 10 mM Tris buffer, and then sonicated in 15 second intervals for a period of 2 minutes. A portion of the crude lysate was then heated at either 56 degrees Celsius (or simply incubated at 37 degrees Celsius) for 30 minutes, as described above. Lysates (50 microliters) were then assayed for the ability to infect a host cell (in the clone 37 assay as described above).

FIG. 1 is a copy of an autoradiograph reflecting hybridization of the CFTR probe to EcoRI-digested DNA isolated from clone 37 cells that had been infected with viral lysates derived from cells carrying constructs of the present invention and control cells as follows: panel #1=293/AAVCFTR cells lipofected with pRS5, in which the rep and cap genes are joined together as they are in wildtype AAV (for each of the numbered panels (1–3), the first lane reflects cells infected with unheated lysate with additional Ad5, the second lane reflects cells infected with heated lysate without additional Ad5, and the third lane reflects cells infected with heated lysate with additional Ad5); panel #2=293/AAVCFTR cells lipofected with mMT1-rep-cap, in which the rep and cap genes are joined together as they are in wildtype; panel #3=293/AAVCFTR cells lipofected with split-packaging plasmids mMT1-rep78 and CMV-cap, in which case the rep and split-cap genes lie on separate plasmids. The intensely-hybridizing band at about 1.5 kb corresponds to the position expected for the internal EcoRI fragment of CFTR (which is 1488 base pairs).

The results in FIG. 1 demonstrate that the use of only AAV split-packaging genes (as in 3) was capable of mediating the production of infectious heat-stable rAAV virus particles as measured in the clone 37 assay; and further revealed that substantially more infectious virus was obtained using the AAV split-packaging constructs (mMT1-rep78 and CMV-cap) as compared to the "standard" rep-cap constructs (pRS5 and mMT1-rep-cap), in which the rep and cap genes are joined together as they are in wild-type AAV.

Example 13
Ability of a Cell Line Comprising Three AAV Split-packaging Genes to Mediate Rescue and Amplification of an Integrated Recombinant AAV Pro-vector and to Generate Heat-stable Infectious Vector Particles Following essentially the same procedures as described above, we introduced additional AAV split-packaging constructs into cells carrying an integrated rAAV vector. In this example, we examined the effect of introducing three AAV split-packaging genes (in particular, a rep78 gene, a rep52 gene and a split-cap gene) into 293/AAVCFTR cells. In addition, the rep52 and split-cap genes were introduced in three different ways: (1) on two different plasmids (mMT1-rep52 and CMV-cap); (2) as a single plasmid comprising rep 52 and split-cap in tandem orientation (as described in Example 4); or (3) as a single plasmid comprising rep52 and split-cap in divergent orientation (as described in Example 5). The positive control was a plasmid with a complete rep-cap cassettes (mMT1-rep-cap as described above). The plasmids (10 micrograms each) were introduced by lipofection, after adenovirus infection, as described above, in the following combinations: (i) mMT1-rep-cap; (ii) mMT1-rep78 and mMT1-rep52 and CMV-cap; (iii) mMT1-rep78 and CMV-cap/mMT1-rep52 (tandem); and (iv) mMT1-rep78 and CMV-cap/mMT1-rep52 (divergent). After a 72 hour incubation, cells were harvested, resuspended in 500 microliters of 10 mM Tris buffer, and then sonicated in 15 second intervals for a period of 2 minutes. A portion of the crude lysate was then heated at either 56 degrees Celsius (or simply incubated at 37 degrees Celsius) for 30 minutes. Lysates (50 microliters) were then assayed for the ability to infect a host cell (in the clone 37 assay as described above).

Figure 2:
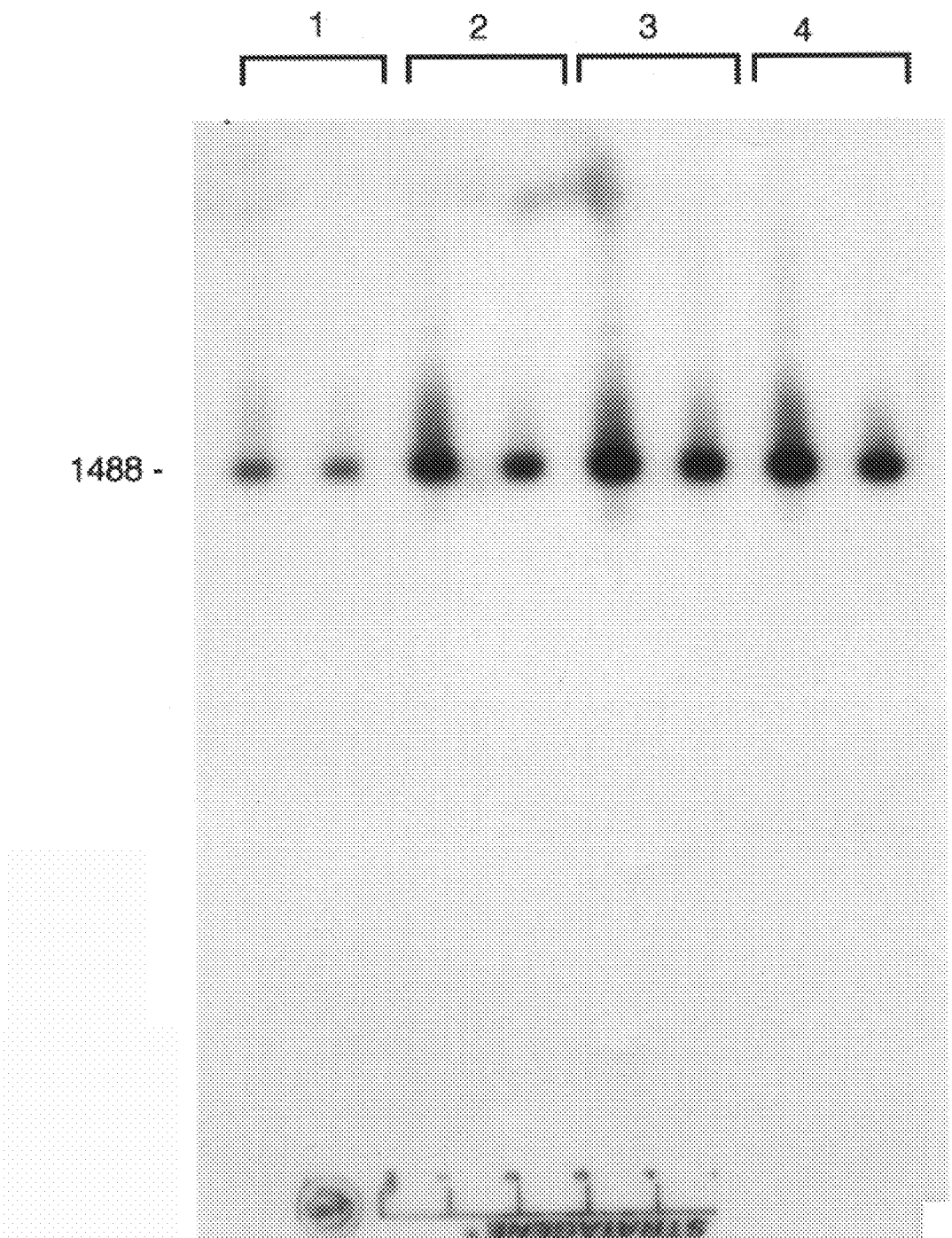
FIG. 2 shows the results of Southern blots indicating that AAV split-packaging genes of the present invention can be used to provide AAV replication and encapsidation functions effective for the production of infectious AAV vector particles useful for delivering a transgene to a target cell, as described in Example 13.

FIG. 2 is a copy of an autoradiograph reflecting hybridization of the CFTR probe to EcoRI-digested DNA isolated from clone 37 cells that had been infected with viral lysates derived from cells carrying constructs of the present invention and control cells as follows: panel #1=293/AAVCFTR cells lipofected with mMT1-rep-cap, in which the rep and cap genes are joined together as they are in wildtype (for each of the numbered panels (1–4), the first lane reflects cells infected with unheated lysate with additional Ad5, the second lane reflects cells infected with heated lysate without additional Ad5, and the third lane reflects cells infected with heated lysate with additional Ad5); panel #2=293/AAVCFTR cells lipofected with mMT1-rep78, mMT1-rep52 and CMVcap, in which case rep52 and cap are provided on separate plasmids; panel #3=293/AAVCFTR cells lipofected with plasmids mMT1-rep78 and CMV-cap/mMT1-rep52 (in which case rep52 and split-cap lie on a single plasmid, CMV-cap/mMT1-rep52, in divergent orientation (as described in Example 5)); panel #4=293/AAVCFTR cells lipofected with plasmids mMT1-rep78 and CMV-cap/mMT1-rep52 (in which case rep52 and split-cap lie on a single plasmid, CMV-cap/mMT1-rep52, in tandem orientation (as described in Example 4)).

The results of FIG. 2 demonstrate that the use of only AAV split-packaging genes (as in (iii)) was capable of mediating the production of infectious heat-stable rAAV virus particles as measured in the clone 37 assay; and again revealed that substantially more infectious virus (at least 10-fold more) was obtained using the AAV split-packaging constructs (mMT1-rep52, and CMVcap, and the CMV-cap/mMT1-rep52 constructs) as compared to the "standard" rep-cap constructs (mMT1-rep-cap) in which the rep and cap genes are joined together as they are in the wild-type AAV.

Example 14
Stable Introduction of an AAV Split-packaging Gene (Rep78) Into a Cell Line Containing a Stably-integrated Recombinant AAV Pro-vector As an illustrative example of the introduction of an AAV split-packaging gene into a cell line containing a stably-integrated rAAV pro-vector, we introduced a rep78 gene into HelaS3/AAVCFTR (as described above). Briefly, the plasmid mMTRep78 was used to introduce the rep78 gene by electroporation, essentially as described above. Selection was performed using G418 (at 1.2 mg/ml) since the plasmid contains a neo resistance gene in the plasmid backbone.

Briefly, HelaS3/AAVCFTR cells were transfected with mMTRep78 (using electroporation as described above). Polyclonal cell lines resistant to G418 were obtained after 10–12 days of drug selection. Individual clones were picked, expanded into clonal populations and tested for the presence of a stable-integrated AAV rep78 gene. Clones were analyzed by Southern analysis to ensure that they contained an intact copy of the rep78 gene. A number of stable integrants, typically comprising from one to several integrated copies of the AAV split-packaging gene, were readily obtained using such techniques. For these examples, we elected to proceed with clones having only a single full-length copy of the AAV split-packaging gene (although clones have multiple integrated copies may well be useful as a means of providing additional sources of the AAV packaging functions).

A resulting cell line, called HelaS3/AAVCFTR/rep78, was found to contain an intact copy of the rep78 gene and was also found to be capable of growth at levels equivalent to the parental-type cells, indicating that the integrated rep78 gene under the control of the heterologous promoter was not significantly deleterious to the host cells.

Example 15
Ability of a Cell Line comprising an Integrated Copy of Rep78 and an Integrated Recombinant AAV Pro-vector to Mediate Rescue and Amplification of the Pro-vector The HelaS3/AAVCFTR/rep78 cell line described above was analyzed for the ability of the cells to mediate rescue and amplification of the rAAV vector. Briefly, the cells were infected with helper virus (adenovirus Ad5) as described above, and, after incubation, Southern analysis was performed to monitor rescue and amplification of the rAAV pro-vector.

The Southern analysis confirmed that the integrated copy of rep78 was capable of mediating rescue and amplification of the rAAV pro-vector (resulting in an EcoRI band migrating at approximately 1.5 kb that hybridized with the radioactively labeled CFTR probe).

Example 16
Introduction of an AAV Split-cap Gene Into a Cell Line Containing a Stably-integrated Recombinant AAV Pro-vector and a Stably-integrated Rep78 Gene The HelaS3/AAVCFTR/rep78 cell line described above was infected with adenovirus, and transfected with a plasmid (CMV-cap) comprising an AAV split-cap gene, as described above. The resulting cells were monitored for the ability to produce infectious AAV vector particles by obtaining cell lysates and performing a clone 37 infectious titer assay as described above.

The results confirmed that the HelaS3/AAVCFTR/rep78 cell line infected with adenovirus and transfected with CMV-cap produced infectious AAV virus that could effectively deliver the CFTR gene to clone 37 cells. Heating the HelaS3 viral lysates (at 56 degrees Celsius for 30 minutes to one hour) was found to inactivate adenovirus present in the preparation, and also reduced the AAV infectious titer of the lysate (i.e. even when adenovirus was added back to the heated lysate, the production of AAV in a subsequent clone 37 assay was reduced).

Example 17
Introduction of an AAV Rep52 Gene and Split-cap Gene Into a Cell Line containing a Stably-integrated Recombinant AAV Pro-vector and a Stably-integrated Rep78 Gene The HelaS3/AAVCFTR/rep78 cell line described above was infected with adenovirus, and transfected with either a pair of plasmids (CMV-cap and mMTRep52) or a single plasmid comprising an AAV split-cap gene (CMV-cap/mMTRep78, divergent orientation), as described above. The resulting cells were monitored for the ability to produce infectious AAV vector particles by obtaining cell lysates and performing a clone 37 infectious titer assay as described above.

The results indicated that the HelaS3/AAVCFTR/rep78 cell line infected with adenovirus and transfected with additional split-packaging genes (split-cap and rep52) produced infectious AAV virus that could effectively deliver the CFTR gene to clone 37 cells. Heating the viral lysates (at 56 degrees Celsius for 30 minutes to one hour) was found to inactivate adenovirus present in the preparation, and did not substantially reduce the AAV infectious titer of the lysate, indicating that the inclusion of both the split-cap gene and the rep52 gene resulted in the production of heat-stable infectious AAV viral particles. It should be noted that, while heat-labile AAV produced as described is also infectious, the ability to produce heat-stable AAV provides an additional advantage in terms of AAV production techniques since heat can be employed to inactivate adenovirus in the preparations without substantially affecting the infectious titer of the AAV produced. Alternatively, or in addition to heat inactivation, the adenovirus can be removed by other means such as purification.

Example 18
Generation of Cell Lines Containing a Stably-integrated Recombinant AAV Pro-vector and Multiple Stably-initegrated AAV Split-packaging Genes As an illustrative example of the generation of a cell line containing a stably-integrated rAAV pro-vector and multiple stably-integrated AAV split-packaging genes, we introduced a rep52 gene and a split-cap gene into a cell line that already contained stably-integrated copies of an rAAV vector and a rep78 gene (HelaS3/AAVCFTR/rep78, as described above). Briefly, the plasmid CMV-cap/mMTRepS52 (divergent orientation) was used to introduce repS52 and split-cap genes into HelaS3/AAVCFTR/rep78 cells by electroporation, essentially as described above. Selection was performed using His-free medium supplemented with 0.5 mM L-histidinol since the plasmid contains an L-histidinol resistance gene in the plasmid backbone, as noted above.

Briefly, HelaS3/AAVCFTR cells were transfected with CMV-cap/mMTRep2 (divergent orientation, as described above). Polyclonal cell lines resistant to L-histidinol were obtained after about 5 days of drug selection. Individual clones were picked, expanded into clonal populations and tested for the presence of stable-integrated copies of the AAV rep52 and split-cap genes. Clones were analyzed by Southern analysis to ensure that they contained an intact copy of the rep52 and split-cap genes. A number of stable integrants, typically comprising from one to several integrated copies of the AAV split-packaging genes, were readily obtained using such techniques. For these examples, we elected to proceed with clones having only a single full-length copy of the AAV split-packaging genes (although clones have multiple integrated copies may well be useful as a means of providing additional sources of the AAV packaging functions). One of the resulting cell lines termed HelaS3/AAVCFTR/rep78/rep52/split-cap was further tested for the ability to rescue and amplify the rAAV pro-vector and to produce infectious AAV viral particles.

Example 19
Ability of a Cell Line Comprising Multiple Stably-integrated AAV Packaging Genes and an Integrated Recombinant AAV Pro-vector to Mediate Rescue and Amplification of the Pro-vector The HelaS3/AAVCFTR/rep78/rep52/split-cap cell line was tested for the ability to mediate rescue and amplification of the integrated rAAV vector upon adenovirus infection, and to produce infectious rAAV virus particles, using techniques as described above. Briefly, the cells were infected with adenovirus and, following incubation, a portion of the cells were used to obtain viral lysates which were tested in the clone 37 assay as described above.

The results of the clone 37 assay indicated that the HelaS31AAVCFTR/rep78/rep52/split-cap cell line infected with adenovirus and transfected with CMV-cap produced infectious AAV virus that could effectively deliver the CFTR gene to clone 37 cells. Heating the HelaS3 viral lysates (at 56 degrees Celsius for 30 minutes to one hour) was found to inactivate adenovirus present in the preparation and also reduced the AAV infectious titer of the lysate (i.e. even when adenovirus was added back to the heated lysate, the production of AAV in a subsequent clone 37 assay was reduced); as discussed above and below.

Example 20
Introduction of Additional Copies of AAV Split-packaging Genes (Rep52 and Split-cap) Into a Cell Line Comprising a Stably-integrated Recombinant AAV Pro-vector and Stably-integrated AAV Split-packaging Genes The HelaS3 /AAVCFTR/rep78/rep52/split-cap cell line described in the preceding example was capable of generating heat-labile but infectious rAAV virus particles as noted above. Based on our previous observations, we suspected that the introduction of additional copies of the split-packaging genes rep52 and split-cap would result in the production of heat-stable AAV particles, which was confirmed experimentally.

Briefly, we transiently transfected additional copies of either the rep52 gene, the split-cap gene, or both, into adenovirus-infected HelaS3/AAVCFTR/rep78/rep52/split-cap cells using procedures as described above. After incubation, viral lysates were obtained and these were examined in a clone 37 assay as described above. The results revealed that when additional copies of both rep52 and split-cap were provided, the cells were capable of producing high titers of heat-stable rAAV particles. In particular, cells comprising additional copies of the AAV split-packaging genes (both split-cap and rep52) produced at least about 10-fold more virus than cells without such constructs and the AAV produced was heat-stable.

Example 21
Testing AAV Packaging Cells for the Ability to Generate Replication-competent AAV ("RCA")

The most preferred AAV packaging cells produced according to the present invention employ only AAV split-packaging genes to provide AAV Rep and Cap proteins. Such packaging cells are capable of producing high titers of infectious rAAV virus particles as described in the preceding examples. However, an additional advantage of using split-packaging systems according to the present invention arises from the fact that the split constructs are much less likely to be capable of generating replication-competent AAV ("rcA" or "rcAAV") particles. This contrasts with a variety of prior-art techniques that can result in the generation of such rcA. Contamination of rAAV production procedures with such particles can potentially result in preferential reproduction of rcA rather than the desired production of replication-incompetent rAAV particles where, as in the case of CFTR, the rAAV vector is larger than the wild-type AAV genome. In contrast, where the AAV packaging functions are completely split, as in preferred examples of the present invention, the generation of rcA is substantially less likely because it would require multiple non-homologous recombination events to reconstitute an AAV genome comprising rep and cap genes capable of providing all of the necessary Rep and Cap proteins, as well as flanking AAV ITR sequences.

Confirmation that the split-packaging systems of the present invention substantially reduce or eliminate the likelihood of generating rcA can be effectively obtained by incubating viral lysates produced using AAV packaging cells (as described above) with human target cells such as parental-type Hela or 293 cells and infecting such cells with adenovirus. Since rcA would presumably be capable of providing AAV Rep and Cap functions, particularly after infection by helper virus, and the Rep proteins could then amplify the rcA genome, infection with rcA would be expected to result in amplified rep and cap sequences in the target cells which could be detected either directly (e.g., using hybridization to labeled rep and/or cap gene fragments) or indirectly (by assaying for gene products of the rep and/or cap genes). Wild-type AAV (e.g., at an MOI of about 0.1 and dilutions serial thereof) can be used as a positive control. Multiple rounds of such infections can be performed as a means of amplifying any potential rcA.

Using split-packaging genes of the present invention, the frequency of generation of rcA is expected to be extremely small (and is likely to be below the levels of detection) because of the number of non-homologous recombination events that would be required to effectively regenerate a replication-competent AAV.

What is claimed is:

1. A composition useful in preparing an adeno-associated virus (AAV) split-packaging cell useful for high efficiency packaging of a recombinant adeno-associated virus (rAAV) vector, said composition comprising:
   (i) a polynucleotide comprising an AAV split-cap gene, wherein said split-cap gene is uncoupled from Rep78-specific sequences of an AAV rep gene, wherein p40 promoter of said split-cap gene is replaced with a first heterologous promoter which is operably linked to said split-cap gene;
   (ii) a polynucleotide comprising an AAV rep78 gene, wherein said rep78 gene is uncoupled from Cap-specific sequences of an AAV cap gene, wherein p5 promoter of said rep78 gene is replaced with a second heterologous promoter which is operably linked to said rep78 gene; and
   (iii) a polynucleotide comprising an AAV rep52 gene, wherein said rep52 gene is uncoupled from Rep78-specific sequences of an AAV rep gene, wherein p19 promoter of said rep52 gene is replaced with a third heterologous promoter which is operably linked to said rep52 gene;
wherein the polynucleotide of (i) and (iii) are a single polynucleotide construct.

2. The composition of claim 1, wherein one of said promoters is an inducible promoter.

3. A method of generating a mammalian cell useful for high efficiency packaging of an rAAV vector, comprising introducing into said cell the composition of claim 1.

4. A method of generating a mammalian cell useful for high efficiency packaging of an rAAV vector, comprising stably introducing into said cell the composition of claim 1.

5. The composition of claim 1, wherein the AAV split-cap gene and the AAV rep52 gene are arranged in tandem transcriptional orientation.

6. The composition of claim 1, wherein the AAV split-cap gene and the AAV rep52 gene are arranged in divergent transcriptional orientation.

7. A mammalian cell generated according to claim 3.

8. A mammalian cell generated according to claim 4.

9. A method of generating a mammalian cell useful for high efficiency packaging of an rAAV vector, comprising contacting said cell with:
   (i) a polynucleotide comprising an AAV split-cap gene, wherein said split-cap gene is uncoupled from Rep78-specific sequences of an AAV rep gene, wherein p40 promoter of said split-cap gene is replaced with a first heterologous promoter which is operably linked to said split-cap gene;
   (ii) a polynucleotide comprising an AAV rep78 gene, wherein said rep78 gene is uncoupled from Cap-specific sequences of an AAV cap gene, wherein p5 promoter of said rep78 gene is replaced with a second heterologous promoter which is operably linked to said rep78 gene; and
   (iii) a polynucleotide comprising an AAV rep52 gene, wherein said rep52 gene is uncoupled from Rep78-specific sequences of an AAV rep gene, wherein p19 promoter of said rep52 gene is replaced with a third heterologous promoter which is operably linked to said rep52 gene;
wherein the polynucleotide of (i) and (iii) are a single polynucleotide construct.

10. A composition useful in preparing an adeno-associated virus (AAV) split-packaging cell useful for high efficiency packaging of a recombinant adeno-associated virus (rAAV) vector, said composition comprising:
   (i) a polynucleotide comprising an AAV split-cap gene, wherein said split-cap gene is uncoupled from Rep78-specific sequences of an AAV rep gene, wherein p40 promoter of said split-cap gene is replaced with a first heterologous promoter which is operably linked to said split-cap gene;
   (ii) a polynucleotide comprising an AAV rep78 gene, wherein said rep78 gene is uncoupled from Cap-specific sequences of an AAV cap gene, wherein p5 promoter of said rep78 gene is replaced with a second heterologous promoter which is operably linked to said rep78 gene; and
   (iii) a polynucleotide comprising an AAV rep52 gene, wherein said rep52 gene is uncoupled from Rep78-specific sequences of an AAV rep gene, wherein p19 promoter of said rep52 gene is replaced with a third heterologous promoter which is operably linked to said rep52 gene;
wherein the first heterologous promoter, the second heterologous promoter, and the third heterologous promoter are different from each other.

11. A mammalian cell useful for high efficiency packaging of a recombinant adeno-associated virus (rAAV) vector, said cell comprising at least one copy of each of the following AAV split-packaging genes:

(i) an AAV split-cap gene, wherein said split-cap gene is uncoupled from Rep78-specific sequences of an AAV rep gene, wherein p40 promoter of said split-cap gene is replaced with a first heterologous promoter which is operably linked to said split-cap gene;

(ii) an AAV rep78 gene, wherein said rep78 gene is uncoupled from Cap-specific sequences of an AAV cap gene, wherein p5 promoter of said rep78 gene is replaced with a second heterologous promoter which is operably linked to said rep78 gene; and (iii) an AAV rep52 gene, wherein said rep52 gene is uncoupled from Rep78-specific sequences of an AAV rep gene, wherein p19 of said rep52 gene is replaced with a third heterologous promoter which is operably linked to said rep52 gene;

wherein the first heterologous promoter, the second heterologous promoter, and the third heterologous promoter are different from each other.

12. A mammalian cell according to claim 11, wherein at least one of said promoters is an inducible heterologous promoter.

13. A mammalian cell according to claim 11, wherein at least one of said AAV split-packaging genes is operably linked to a heterologous enhancer.

14. A mammalian cell according to claim 11, wherein at least one of said AAV split-packaging genes is stably integrated into said cell.

15. A mammalian cell according to claim 11, wherein at least two different AAV split-packaging genes are stably integrated into said cell.

16. A mammalian cell according to claim 11, wherein all three AAV split-packaging genes are stably integrated into said cell.

17. A mammalian cell according to claim 11, further comprising a recombinant AAV vector.

18. A mammalian cell according to claim 17, wherein said recombinant AAV vector comprises a therapeutic gene.

19. A mammalian cell according to claim 18, wherein said therapeutic gene encodes a cystic fibrosis transmembrane regulator.

20. A mammalian cell according to claim 11, wherein said mammalian cell is a human cell.

21. A method of generating a mammalian cell useful for high efficiency packaging of an rAAV vector, comprising contacting said cell with:

(i) a polynucleotide comprising an AAV split-cap gene, wherein said split-cap gene is uncoupled from Rep78-specific sequences of an AAV rep gene, wherein p40 promoter of said split-cap gene is replaced with a first heterologous promoter which is operably linked to said split-cap gene;

(ii) a polynucleotide comprising an AAV rep78 gene, wherein said rep78 gene is uncoupled from Cap-specific sequences of an AAV cap gene, wherein p5 promoter of said rep78 gene is replaced with a second heterologous promoter which is operably linked to said rep78 gene; and (iii) a polynucleotide comprising an AAV rep52 gene, wherein said rep52 gene is uncoupled from Rep78-specific sequences of an AAV rep gene, wherein p19 promoter of said rep52 gene is replaced with a third heterologous promoter which is operably linked to said rep52 gene;

wherein the first heterologous promoter, the second heterologous promoter, and the third heterologous promoter are different from each other.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (xi) SEQUENCE DESCRIPTION: SEQ ID NO: 1:

CTAGACCTCC TCAGATTAGC GAGGGGCCAT AGCTTATGAG CTAGCCGC           48